(12) United States Patent
Meruelo et al.

(10) Patent No.: US 7,378,272 B2
(45) Date of Patent: May 27, 2008

(54) PACKAGING CELL LINES FOR THE CONTINUOUS PRODUCTION OF ALPHAVIRUS VECTORS

(75) Inventors: Daniel Meruelo, Scarborough, NY (US); Christine Pampeno, New York, NY (US)

(73) Assignee: New York University, New York, NY (US)

( * ) Notice: Subject to any disclaimer, the term of this patent is extended or adjusted under 35 U.S.C. 154(b) by 87 days.

(21) Appl. No.: 10/473,482

(22) PCT Filed: Mar. 27, 2002

(86) PCT No.: PCT/US02/09431

§ 371 (c)(1), (2), (4) Date: Sep. 26, 2003

(87) PCT Pub. No.: WO02/077221

PCT Pub. Date: Oct. 3, 2002

(65) Prior Publication Data

US 2004/0115789 A1    Jun. 17, 2004

Related U.S. Application Data

(60) Provisional application No. 60/279,048, filed on Mar. 27, 2001.

(51) Int. Cl.
*C12N 15/00* (2006.01)
*A61K 39/12* (2006.01)

(52) U.S. Cl. .................. 435/320.1; 424/218.1
(58) Field of Classification Search ............ 435/320.1, 435/325, 326, 69.1; 424/218.1; 536/23.1, 536/24.3
See application file for complete search history.

(56) References Cited

U.S. PATENT DOCUMENTS 5,789,245 A    8/1998  Dubensky, Jr. et al.
6,943,015 B2 *  9/2005  Frolov et al. ............ 435/320.1

OTHER PUBLICATIONS

Hertz et al. Host-dependent evolution of the sindbis virus promoter for subgenomic mRNA synthesis, Journal of Virology, 1995, 69(12):7775-7781.*
Theilmann et al, Molecular analysis of the trans-activating IE-2 gene of *Orgyia pseudotsugata* multicapsid nuclear polyhedrosis virus, Virology, 1992, 187:84-96.*
Polo et al, "Stable Alphavirus Packaging Cell Lines for Sindbis Virus and Semliki Forest Virus-Derived Vectors," *Proc. Natl. Acad. Sci.* USA, Apr. 1999, vol. 96, pp. 4598-4603.

* cited by examiner

*Primary Examiner*—Stacy B. Chen
(74) *Attorney, Agent, or Firm*—Darby & Darby

(57) ABSTRACT

The present invention pertains to packaging cell lines useful for the production of viral vectors, particularly packaging cell lines for continuous production of Sindbis viral vectors at high efficiency. The packaging cell line comprises an insect cell having DNA that encodes alphavirus structural proteins, replicase and a replicon.

28 Claims, 15 Drawing Sheets

Vector vary in their targeting capabilities as described in the text.
Both confer blasticidin resistance.

Concentrated ↑   Unconcentrated ↓

PACKAGING CELL LINES FOR THE CONTINUOUS PRODUCTION OF ALPHAVIRUS VECTORS

This application claims priority under 35 U.S.C. § 119(e) from Provisional Application Ser. No. 60/279,048, filed Mar. 27, 2001.

The United States Government has certain rights to this invention by value of funding received from Grant No. CA 68498 from the National Cancer Institute (NCI).

FIELD OF THE INVENTION

The present invention pertains to packaging cell line useful for the production of viral vectors. In particular, the present invention pertains to packaging cell line for continuous production of Sindbis viral vectors.

BACKGROUND OF THE INVENTION

Cancer gene therapy would benefit greatly from the availability of a vector that has a high efficiency of gene expression and the ability to target tumors. A number of transfection systems have been developed to deliver heterologous genes into tumors in vivo to investigate cancer gene therapy, but all have limitations. For example, retroviral vectors have been used for gene delivery because they mediate stable gene transfer with a low potential for immunogenicity; however, transfer efficiencies are relatively low (1-4) and germ line modification is a potential problem (5). In addition, retroviral vectors, with few exceptions, are susceptible to lysis by serum components in human blood (6-8). This greatly limits their in vivo applications. Adenoviral vectors appear to be more efficient for gene transfer in vivo, but these vectors may cause toxicity to patients due to the highly immunogenic properties of adenoviral proteins (9, 10). Additionally, they are commonly used in a localized manner because they generally lack the ability to be delivered via the bloodstream (11-13). In fact, they may cause severe toxicity if administered intravenously (77).

An alternative viral vector system that has numerous advantages is based on Sindbis virus. Sindbis virus has been studied extensively since its discovery in Egypt in 1953 (14-16, 69). Gene transduction based on Sindbis virus, a member of the alphavirus genus, has been well-studied (17-27). Sindbis vectors show extremely high efficiency of gene transfer. They are plus-strand RNA viruses, which through a process of amplification in the cytoplasm of infected cells can express $10^5$ active RNA species per cell within a few hours after infection. This level of RNA amplification allows for very high levels of expression of the transferred gene product, which would allow for prolonged expression were it not for the apoptotic nature of the virus (28-31).

Based on recommendations for the handling of alphaviruses and other arboviruses in the laboratory (32), Sindbis virus is considered fairly safe. Sindbis virus is endemic to many parts of the world where it is associated with minimal, transient disease (17, 33, and 34). Whereas the majority of alphaviruses require Level 3 practice and containment and/or vaccination, Sindbis requires only Level 2. Level 2 practice and containment is assigned to viruses whose infection results either in no disease or in disease that is self-limited (32, 33, 34). Replication incompetent Sindbis vectors derived from Sindbis viruses, such as those referred to herein, can be considered even safer as their capacity to infect and replicate to cause viremia or disease is virtually non-existent. It has been stated that they can be considered safe enough for level 1 use (ACGM Compendium Of Guidance. Guidance From The Health And Safety Commission's Advisory Committee On Genetic Modification. Part 2—Annex III—Guidance On Commonly Used Viral Vectors, issued March 2000. Available on the Worldwide Web at hse.gov.uk. The capacity to infect and replicate to cause viremia can only be reacquired through recombination, which can be minimized and monitored.

Sindbis vectors also avoid potential complications associated with chromosomal integration (27). Recent methods have added substantial ease to engineering new Sindbis vector constructs capable of nonreplicative infection and further enhanced safety aspects of the vector (17). Because Sindbis virus is a blood-borne virus (33) and can cross the blood brain barrier (18), vectors based on this virus are among the few available ones that are capable of migrating through the bloodstream to reach all cells of the body. In this respect they hold an important advantage over many other vectors. Table 1 contrasts a number of gene delivery agents with Sindbis and shows some of the distinctive advantages of vectors made from this virus.

TABLE 1

| Vector | Easy to engineer | Easy to Produce | Can be produced in titers >$10^8$ w/o concentration | Not lysed by human serum | No potential for causing cancer in patients | Length of insert sufficient to accommodate most genes | No adverse/ severe immune likely | Capable of infecting >90% of cells | Capable of efficiently targeting specific cells | Capable of infecting all desired cells |
|---|---|---|---|---|---|---|---|---|---|---|
| Targetable Sindbis virus | ☐ | ☐ | ☐ | ☐ | ☐ | ☐ | ☐ | ☐ | ☐ | ☐ |
| AAV | ☐ | | ☐ | ☐ | ☐ | | ☐ | | | |
| Adenovirus | | ☐ | ☐ | ☐ | ☐ | ☐ | | ☐ | | |
| Retroviruses | ☐ | ☐ | | | ☐ | ☐ | | | | |
| Herpesvirus | | | | ☐ | | ☐ | | | | |
| Liposomes | ☐ | | | ☐ | ☐ | ☐ | | | | |
| Naked DNA | ☐ | ☐ | | ☐ | ☐ | ☐ | | | | |

Copending, commonly assigned application Ser. No. 60/279,051, filed Mar. 27, 2001 discloses in vivo studies showing that Sindbis vectors can be used to treat experimental tumors growing in animals and that such treatments can cause substantial necrosis and, in at least one model system, complete elimination of rapidly growing tumors. In addition, it has been shown that Sindbis vectors can be made to target specific cells in vivo and in vitro. Such targeting can be extremely efficient, achieving expression in vitro of a delivered gene in greater than 90% of the targeted cells (35). A number of other laboratories have shown utility for these vectors for the treatment of various conditions (24-27).

Application of viral-based vectors for gene therapy requires efficient processes for their large-scale manufacture. A major obstacle preventing widespread use of Sindbis vectors for gene therapy has been the inability to produce these vectors easily from packaging cell lines. To understand the issues involved in the case of Sindbis vectors, it is important to analyze how these vectors are produced.

Generally, recombinant Sindbis virus is currently produced by the electroporation of two RNA genomes that are synthesized in vitro. One genome, the replicon, directs the synthesis of the gene of interest along with the Sindbis RNA replicase (FIG. 1). This genome also contains a packaging signal allowing it to be incorporated into virion particles by the Sindbis structural proteins. The second, a helper genome (or for greater safety two split structural helper genes; FIG. 2), direct(s) the synthesis of viral structural proteins but lack(s) a packaging signal so that recombinant viral particles will undergo only one round of infection.

FIG. 1 shows the packaging of replication defective replicons by cotransfection of defective-helper RNAs (DHRNAs) expressing the alphavirus structural proteins and the replicon. DHRNAs are designed to contain the cis-acting sequences required for replication as well as the subgenomic RNA promoter driving expression of the structural genes. Packaging of SIN replicons is achieved by efficient cotransfection of cells with both RNAs by electroporation. Replicase/transcriptase functions supplied by the vector RNA lead not only to its own amplification but also act in trans to allow replication and transcription of helper RNA. This results in synthesis of structural proteins that can package the replicon with greater than $10^7$ infectious particles per ml being produced after only 48 h.

In addition to the need to prepare RNA in vitro and electroporate this RNA into cells, the lethality of Sindbis virus requires that this procedure be done anew each time virus is to be produced. In mammalian cells, apoptosis caused by Sindbis virus results in lethality to the infected cells, making it impossible to propagate Sindbis virus infected cells for long periods. To overcome the lethality issue one could construct an inducible system, which would allow propagation of the cells into high numbers before virus production is induced. While the producing cells would still die within days after induction, with an inducible system it would be possible to make large amounts of virus (such as would be needed for clinical applications). By simply preparing large amounts of uninduced cells and freezing aliquots, one could generate a master cell bank from which aliquots could be defrosted as needed, grown to large numbers, and induced to produce virus.

FIG. 2 shows the cotransfection of two DHRNAs along with the expression replicon. One DHRNA (helper 1) expresses the capsid protein and a second DHRNA (helper 2) is designed for high level expression of the virion glycoproteins. Helper 2 uses a deleted version of the capsid-protein that is still able to function as a translational enhancer and an autoprotease but is defective for packaging. This approach is favored because it greatly reduces the possibility that replication competent viruses will arise by recombination. Figure shown is adapted from reference 36.

Polo et al. (37) have developed a "stable" alphavirus packaging cell line using a modification of the two helper system that partially but not fully resolves the need to transfect RNA for vector production. Polo et al. (37) describe the use of an inducible cell system which stably encodes DNA for production of the viral structural proteins, but not the replicon and gene of interest. In this system, translation of the structural proteins (from helpers 1 and 2) is obtained only after synthesis of an authentic subgenomic mRNA by the vector-encoded replicase proteins (which are not encoded by the cells and must be electroporated).

Because the replicon is not present in the packaging cells, to obtain vector production, the Polo et al. (37) system requires electroporation of all the cells with RNA encoding the Sindbis replicon and desired gene. To a large extent this requirement imposes an unnecessary burden in the production of recombinant Sindbis vector for therapeutic application. In particular, given the instability of RNA molecules, large-scale production of in vitro Sindbis RNA genomes is difficult and costly. Further, a complete master cell bank cannot be generated. As Polo et al. (37) must have been aware of this drawback, it is assumed that Polo et al. (37) were not able to design their system in such a way that they could prevent the expression of replicon genes. A reason for not being able to stably integrate the DNA encoding the Sindbis replicon is that production of genes encoded in the replicon, such as nsP2, may be very toxic to mammalian cells.

Therefore, what is needed in the art are packaging cell lines for the production is Sindbis viral vectors which overcome the deficiencies.

SUMMARY OF THE INVENTION

The present inventors have unexpectedly discovered cell lines that can be used for the continuous production of high titered alphavirus vectors.

In one aspect, the present invention provides a packaging cell line for the continuous production of alphavirus vectors comprising an insect cell transfected with DNA encoding the alphavirus structural proteins, replicase, a gene encoding a protein of interest and an alphavirus packaging signal wherein said genes are driven by strong insect promoters and said cell line continuously produces alphavirus viral vectors at a high efficiency.

In another aspect, the present invention provides a method for producing alphavirus vectors comprising the steps of incubating insect cells transfected with DNA encoding the alphavirus structural proteins, replicase, a gene encoding a protein of interest and an alphavirus packaging signal wherein said genes are driven by strong insect promoters in an appropriate selective media and collecting alphavirus vectors secreted into the media.

These and other aspects of the present invention will be apparent to those of ordinary skill in the art in light of the present specification, claims and drawings.

DETAILED DESCRIPTION OF THE INVENTION

Figure 1:
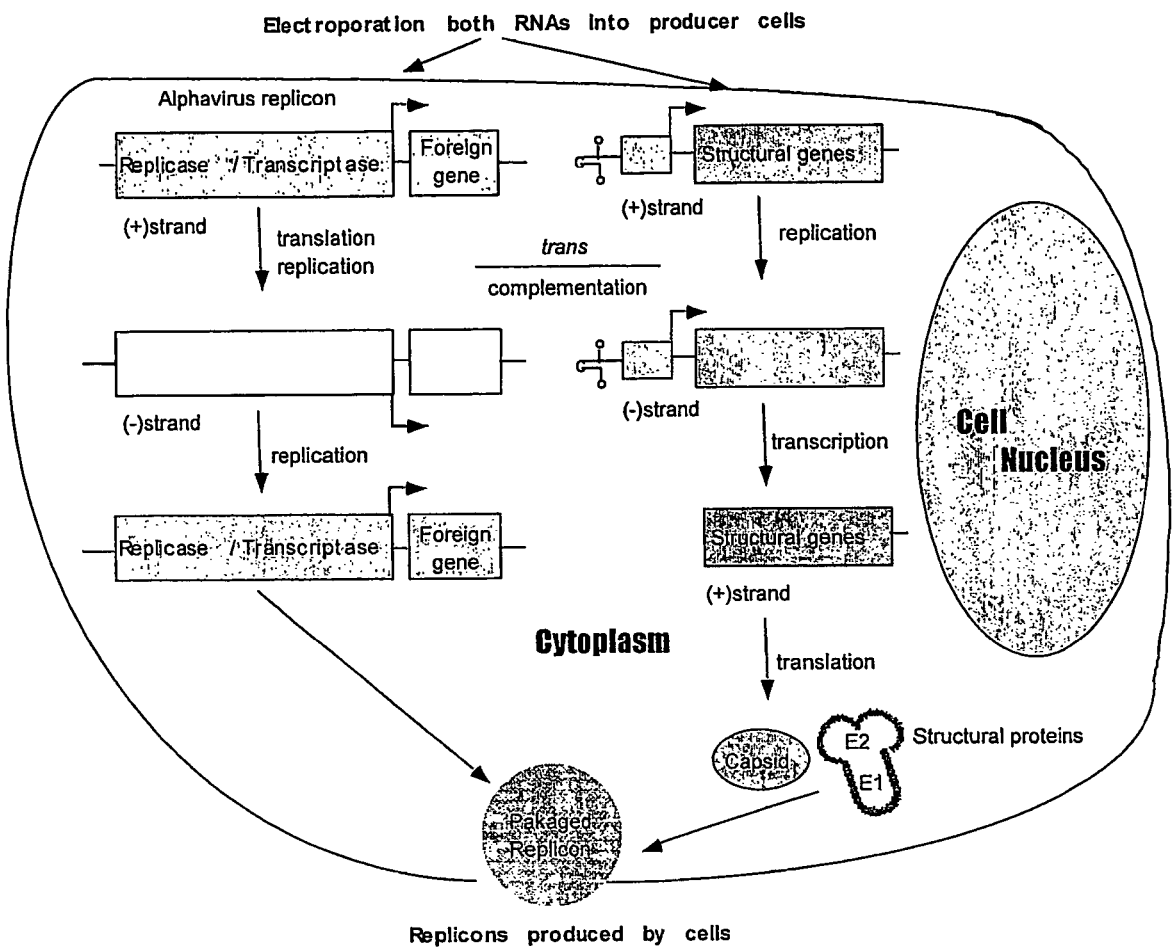
FIG. 1. Packaging of replication-defective replicons by cotransfection of defective-helper RNAs (DHRNAs) expressing the alphavirus structural proteins and the replicon. DHRNAs are designed to contain cis-acting sequences required for replication as well as the subgenomic RNA promoter driving expression of the structural genes. Packaging of replicons is achieved by efficient cotransfection of cells with both RNAs by electroporation. Replicase/transcriptase functions supplied by the vector RNA lead not only to its own amplification but also act in trans to allow replication and transcription of helper RNA. This results in synthesis of structural proteins that can package >$10^7$ infectious particles per ml after only 16-24 h. Figure shown is adapted from reference 36.

Presented herein is methodology which resolves an outstanding block to the clinical use of Sindbis vectors for therapeutic applications. The ability to produce Sindbis vectors from continuous cultures has been greatly hindered by the apoptosis-inducing potential of this virus. Mammalian cells infected by these vectors undergo rapid apoptosis, precluding their use for the continuous production of Sindbis vectors. Furthermore, the approach currently used, which involves in vitro transcription of Sindbis plasmids to produce vector RNA followed typically by electroporation of BHK cells only allows vector harvesting from culture supernatant for only a few (one or two) days. This approach is labor intensive, costly and impractical for large-scale use.

In an effort to overcome these limitations, insect cells have been used, preferably the C6/36 mosquito cell line (available from the American Type Culture Collection, ATTC, Manassas, Va. as ATCC CRL 1660) for vector production. These cells are substantially resistant to the apoptosis-induced properties of Sindbis vectors and can be engineered to establish long-term vector producing cultures. While concerns regarding vector titers of persistently producing cells remain real, it appears that acceptable virus titers can be produced for protracted periods of time using these cells and the methods described herein.

Sindbis virus for use in the present invention can be obtained from any source, including isolates of naturally occurring virus or deposits of viral stocks. Sindbis is commercially available from ATCC under Accession Nos. VR-68, VR-1248 and VR-1248 CAF.

Similarly, any insect cell line, whether derived from primary cells or a cultured cell line, can be used for packaging Sindbis Vectors. In a specific embodiment, a mosquito C6/36 cell line is used. Non-limiting examples of other cell lines for use in the present invention include mosquito u4.4 cells (described in 72), High Five™ cells (Invitrogen Corp., Carlsbad, Calif.), Schneider's *Drosophila* cell line 2 (ATCC Accession # CRL-1963), *Spodoptera frugiperda* SF9 cells (ATCC Accession No. CRL-1711), BHKSIN LUC2 cells (ATCC Accession No. CRL-12201) and C7-10 cells (described in 73).

The packaging cell lines of the present invention are stably transformed with DNA encoding the Sindbis genes required for the production of Sindbis viral vectors. These genes are preferably contained on at least two plasmids. The construction of these cell lines is shown in Example 2 below. One exemplary plasmid, SinRep/LacZ, contains the Sindbis packaging signal, nonstructural protein genes (NSP1-4) for replicating the RNA transcript and the gene of interest, and is a Sindbis virus based expression vector. This plasmid contains the Sindbis replicon and the gene to be transferred and is generically referred to as the SinRep 5-X fragment, wherein X is the gene to be transferred. This strand is packaging cell line positive because it is packaged into progeny vectors. The second exemplary plasmid DHBB is a parental helper plasmid that contains genes for the structural proteins (capsid, E3, E2, 6K and E1), required for packaging of the Sindbis viral genome. This strand is termed packaging signal negative because its genome is not incorporated into the vector. These genes can be obtained from Invitrogen (Carlsbad, Calif.) or isolated from mRNA in cells replicating Sindbis virus. The complete sequence of Sindbis virus has been known for at least 17 years (17).

It is preferable to use strong insect cell promoters to drive the high level constitutive expression of the genes to be expressed in insect cells. The term "strong insect cell promoters" means that the promoter supports high levels of expansion in insect cells (relative to other genes expressed by insect cells). Such a promoter may be, but need not be, endogenous to insect cells. Preferably, the promoter is an insect cell promoter. "High level" constitutive production is defined herein as at least preferably $10^4$ RNAs per cell and most preferably at least $10^5$ RNAs per cell. One such a promoter is the OpIE2 promoter (Orgyia pseudotsugata immediate early 2-promoter). This promoter provides high-level constitutive expression of genes in insect cells. This promoter is also present in the plasmids commercially available from Invitrogen. Other examples of strong cell promoters are for use in the present invention.

Silkmoth (Bombyx mori) cytoplasmic actin gene promoter [available from Invitrogen];

Drosophila AC5 actin gene promoter (high-level constitutive expression) [available from Invitrogen];

Drosophila DS47 gene promoter (moderate-level constitutive expression) [available from Invitrogen];

Drosophila Meigen heat shock protein 70 (hsp70) promoter (strong).

Early to late (ETL) and very late (VL) promoters of AcMNPV [available from Invitrogen];

Murine triacylglycerol hydrolase promoter (78)

The invention will be better understood by reference to the following Examples, which illustrate the invention but are not limiting.

In practicing the present invention, an insect cell, preferably a mosquito cell, is transfected with the two plasmids mentioned above. The cells can be transfected with each plasmid separately or substantially simultaneously. The transfected cells are cultured in selective media and the vectors are secreted into the media wherein they can be collected and stored or concentrated as described below.

The present invention is described below in working examples which are intended to further describe the invention without limiting the scope thereof.

The present invention uses insect cells to produce Alphavirus vectors. Preferably, the insect cell is a mosquito cell and the Alphavirus is Sindbis virus. In the disclosure below, the invention is described with specific reference to Sindbis virus. It should be realized that the invention is directed to the use of Alphavirus vectors. Alphaviruses include Sindbis, Semliki Forest virus, Venezuelan Equine Encephalitis virus and related species (see Strauss and Strauss, Microbiol. Rev., 1994, 58:491-562, Table 1, p. 4937.

The rationale for the use of mosquito cells in particular stems from the differing effects that Sindbis virus has after infection on mosquito cells and mammalian cells. Sindbis infection of most vertebrate cell lines results in massive cell death within 12 to 96 h. By contrast, infection of mosquito cells is often (but not always) accompanied by little if any cytopathology (38-43). In mosquito cells the infection begins with an early acute phase, during which large amounts of virus are shed into the medium and some transient cellular changes occur (38-43). This stage is followed by a prolonged persistent phase in which virus production is maintained at significantly lower levels and the cells continue to grow, divide and produce virus through many passages (38-43). As there is considerable variability in degree of cytopathology, care must be used in the selection of mosquito cells for manufacturing purposes.

One reason why mosquito cells lines have not been thought of for the generation of packaging cell lines, has to do with the frequently reported observation that, over time, titers of virus in mosquito cells drop significantly (38-43). Studies with replication competent virus (39) have indicated that persistently infected cells such as C6/36 produced Sindbis virus at very low levels (less than $10^3$ PFU/ml/day) (39). The decrease of virus production is thought to result from the release by mosquito cells of a polypeptide factor that downregulates virus production (39, 41, 43, 44, 70). One anti-Sindbis factor has been purified and found to be a hydrophobic polypeptide of 3,200 Da However, as will be explained below the situation for production of replication incompetent virus is even more problematic than the drop in titers suggests. To understand why this may be so, one needs to examine how the persistent state is maintained for cells infected with replication competent Sindbis virus. Upon primary infection of mosquito cells, vigorous virus replication occurs in all cells and a large amount of virus is shed into the medium (39, 41, 43, 44). This is possible because the initial replication of the virus allows the infection to propagate from cell to cell. However, during the persistent infection only a fraction of the cells are actively replicating virus at any time. Thus, only a small percentage of the cells contain sufficient viral structural proteins to be detectable in an immunofluorescence assay and further, upon cloning of individual cells from the persistently infected population, only a fraction of the cell clones produce virus (39, 41, 43, 44). Thus, it appears that upon virus infection of mosquito cells, all cells initially support virus replication but a large fraction of cells subsequently stop replicating virus (39, 41, 43, 44). At first, such nonreproducing cells may remain resistant to superinfection, but ultimately the cells may become sensitive to reinfection by virus in the medium or by residual viral RNA in the cell, and in this way the culture remains persistently infected (39, 41, 43, 44). Thus, at any point, the majority of cells in the culture have stopped replicating virus while others have just begun and the rest are somewhere in between.

A model in which a buildup of a viral trans-acting protease leads to the shutoff of minus-strand RNA synthesis followed by the decay of viral replicases producing plus strand RNA has been postulated to explain this phenomenon (39,41,43,44). It has been shown that the uncleaved P123 protein is required for the production of minus-strand RNA templates and that if P123 is cleaved too rapidly by the protease present in nonstructural protein nsP2, minus strand production does not take place (17, 39-44). Since minus strands are the first templates needed for RNA replication, this effectively means that no RNA replication can take place after infection and the appearance of sufficient trans-acting nsP2 protease to rapidly cleave P123. Existing minus strands can continue to be used as a template to produce plus strand RNA but these strands eventually disappear from the cytoplasm. This mechanism is thought to have evolved in order to regulate RNA replication such that minus-strand RNA is only produced early in infection but may also serve to exclude superinfecting virus.

If one envisions attempting to obtain a persistently producing vector packaging cell line with a replication defective Sindbis vector, one might conclude that the situation is impossible, since the benefit of reinfection of the culture by virus emanating from the few producing cells is not possible. Hence as cells become permissive once again, presumably through elimination of viral RNA, they fail to meet replication competent vectors from neighboring cells that would allow them to become reinfected. Under these circumstances it might be envisioned that vector titers would drop not only to very low levels but to zero.

Other complicating factors are the observations that different cell lines derived from mosquitoes exhibit wide variations in their ability to support virus replication in vitro, in their manner of virus production (e.g. secreted into the culture medium or produced internally), the extent of cytopathology associated with the acute phase of infection, and many other relevant parameters (39-44). Thus, any attempt to develop a packaging cell line from mosquitoes cells would appear a daunting problem that must overcome a number of intrinsic technical difficulties, as well as the notion that vector titers might be expected to drop to zero during the persistent phase of the infected state.

A model has been proposed in which a buildup of viral trans-acting protease leads to the shutoff of minus-strand RNA synthesis followed by the decay of viral replicases producing plus strand RNA (39). The present inventors realized that this situation could be overcome by the use of plasmids driven by promoters that are constitutively expressed. In this approach, DNA is driving expression and thus minus-RNA strand degradation has no impact on expression. Such packaging cells are not subjected to the loss of expression, followed by "cure," followed by reinfection from the few producing cells in the culture.

In this strategy a superinfection block can actually increase safety. Any recombination event leading to the production of wild-type virus would, under normal circumstances, produce virus capable of, at least transiently, being expressed by the entire culture. Such an event would ultimately give rise to a persistently infected culture budding out wild type virus that may infect patients receiving vectors made from such cultures. However, as cells expressing Sindbis vectors cannot be superinfected, cultures in which 100% of the cells are producing vectors would not be expected to support superinfection by wild type recombinant viruses. Thus, while recombinations can still be expected to occur, and screening for such viruses must still be done, an additional safety factor is introduced by a block to superinfection. Like splitting genomes to reduce the likelihood that recombinants arise and propagate in the culture, every strategy that decreases the propagation of potential viral replication provides an added margin of safety.

The term "purified" refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. Purity can be evaluated by chromatography, gel electrophoresis, immunoassay, composition analysis, biological assay, and other methods known in the art.

"Continuous production" of the alphavirus vectors of the present invention is defined herein as production for at least 10 days.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B.Perbal, *A Practical Guide To Molecular Cloning* (1984); F. M. Ausubel et al. (eds.), *Current Protocols in Molecular Biology*, John Wiley & Sons, Inc. (1994).

Molecular Biology—Definitions

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense strands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include introns and regulatory DNA sequences, such as promoter sequences, 5'-untranslated region, or 3'-untranslated region which affect for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control of" or "operatively associated with" transcriptional and translational control sequences in a cell when RNA polymerase transcribes the coding sequence into mRNA, which is then trans-RNA spliced (if it contains introns) and translated, in the case of mRNA, into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. In the practice of this invention, vectors can encode alphavirus, particularly Sindbis virus, structural proteins or RNA molecules that make up an alphavirus, particularly Sindbis virus, replicon. Exemplary vectors are depicted in FIGS. 12-15. The invention contemplates vectors constructs, e.g., having the components and orientation of the plasmids in FIGS. 12-15. Note that the genes of interest (lacZ and hygno EGFP in the vectors of FIGS. 13 and 15, respectively) are illustrative; any gene of interest could be introduced into vectors having similar components and orientation.

Vectors typically comprise the nucleic acid (DNA or RNA) of a transmissible agent, into which foreign DNA or RNA is inserted. In the case of DNA, a common way to insert one segment of DNA into another segment of DNA involves the use of enzymes called restriction enzymes that cleave DNA at specific sites (specific groups of nucleotides) called restriction sites. A "cassette" refers to a coding sequence or segment of DNA or RNA that codes for an expression product that can be inserted into a vector at defined sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." DNA, usually of bacterial origin, that can readily accept additional (foreign) DNA and which can readily introduced into a suitable host cell.

Vectors can also be composed entirely of RNA. RNA vectors are usually of viral origin, such as alphavirus disclosed herein.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

EXAMPLES

Presented below is the methodology used to develop permanent mosquito cell lines that lead to the continuous production of replication defective Sindbis vectors at persistently high titers without any associated cytopathology. Also presented are data obtained with such cultures.

Vector Design

Figure 2:
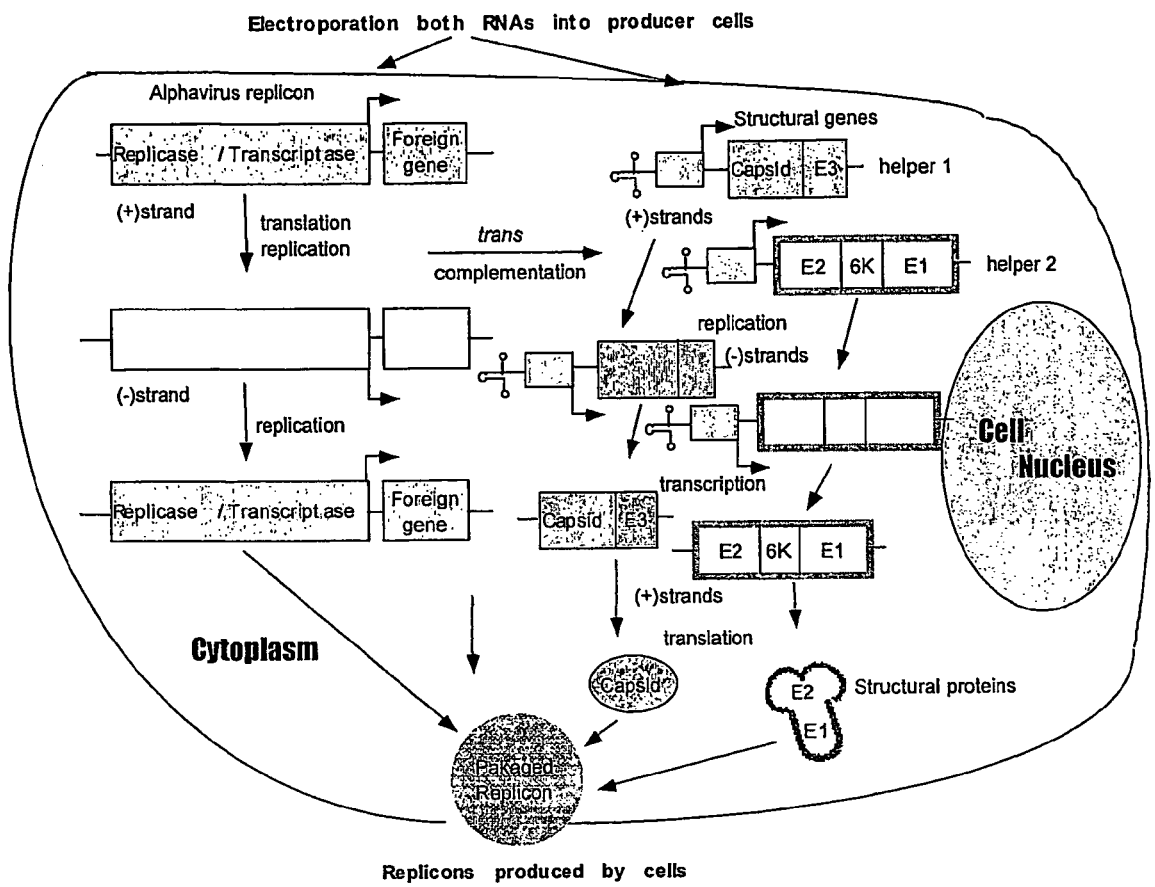
FIG. 2. Cotransfection of two DHRNAs along with the expression replicon. One DHRNA (helper 1) expresses the capsid protein and a second DHRNA (helper 2) is designed for high level expression of the virion glycoproteins. Helper 2 uses a deleted version of the capsid-protein that is still able to function as a translational enhancer and an autoprotease but is defective for packaging. This approach is favored because it greatly reduces the possibility that replication competent viruses will arise by recombination. Figure shown is adapted from reference 36.
Figure 3:
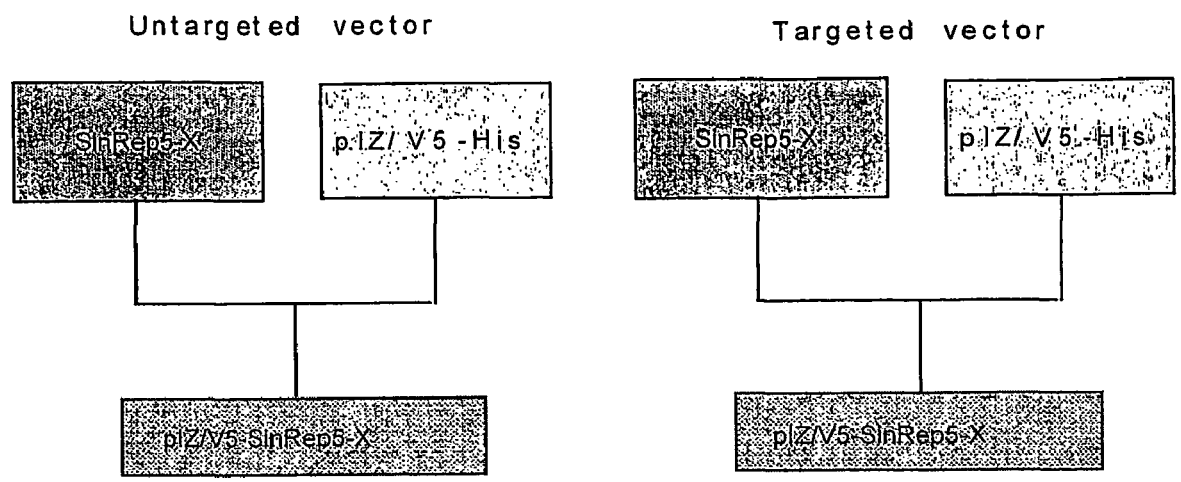
FIG. 3. Schematic representation of the main components of DNA Sindbis vectors capable of expression in mosquito cells (replicon/gene of interest strand). Both targeted and untargeted vectors are the same and confer zeocin resistance. X can be any gene such as LacZ, p53, Hygro-EGFP, etc.
Figure 4:
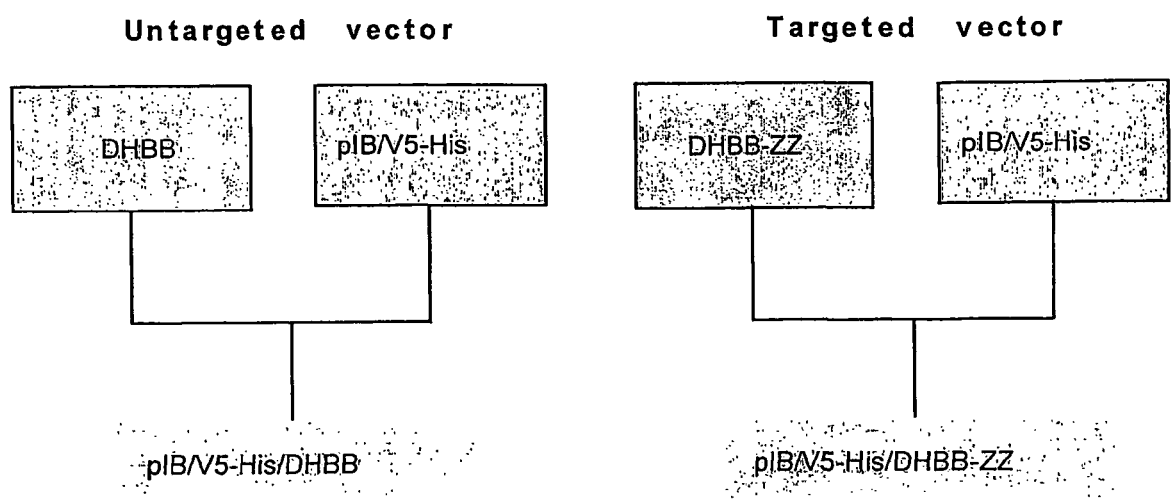
FIG. 4. Schematic representation of the main components of DNA Sindbis vectors capable of expression in mosquito cells (helper strands). Both targeted and untargeted vectors confer blasticidin resistance.
Figure 5:
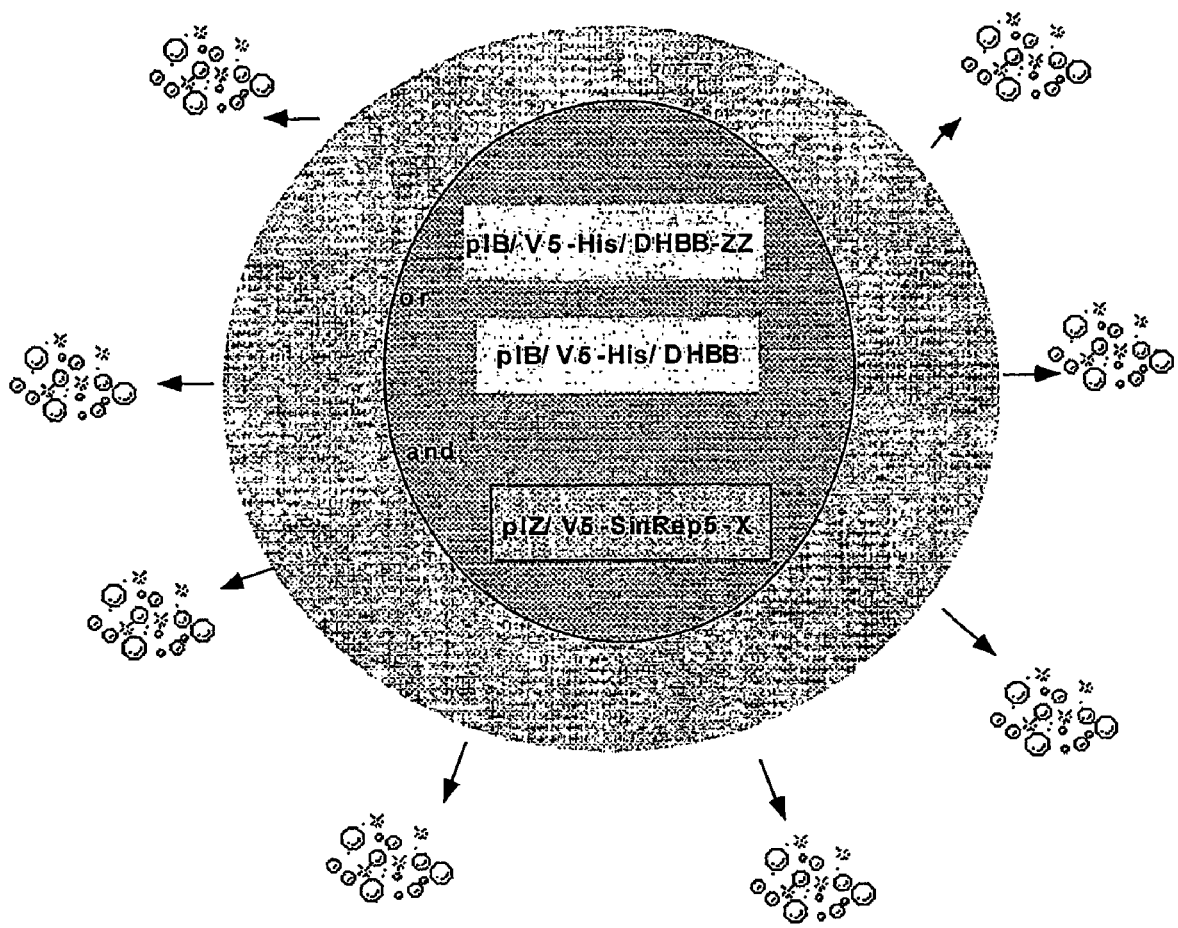
FIG. 5. Schematic representation of Sindbis vector packaging cell line of the present invention.

Two general types of vector constructs are described, one that targets cells on the basis of Protein A-antibody-cell surface antigen expression (or receptor-ligand interactions) and one which targets cells expressing the high-affinity laminin receptor (57, 58, 67). Each of these vectors can be used to introduce any desired gene into selected cells. Common to both vectors is the SinRep5-X fragment, which encodes the Sindbis replicon and the desired gene (X) to be transfected (FIG. 3). This strand is packaging cell positive so that it can be incorporated into progeny vectors made from the producing packaging cell line. The second strand differs depending on whether the vector is targetable via Protein A-IgG interactions (or ligand-receptor interactions) with specific cells, or merely recognizes the high-affinity laminin receptor present on cells to be infected (FIG. 2). Although the latter has not been modified with respect to targeting, many investigators have showed that the high affinity receptor is not expressed equally on all cells (45-55, 59-66). The laminin receptor recognizing vector, known as DHBB/SinRep5-X, comprises the helper strand (DHBB) carrying the conventional Sindbis structural genes. This strand is packaging signal negative so its genome is not incorporated into the vectors produced, thereby rendering the progeny vectors replication incompetent. The Protein A-IgG, targetable vectors contain the Protein A modified helper strand DHBBZZ. It is also packaging cell negative.

Example 1

Selection of Cells for the Generation of Recombinant Sindbis Vector Packaging Cell Line Several insect cell lines (*A. albopictus*-derived C6/36 [ATCC Accession # CRL-1660], C7-10 cells (described in 73)], and u4.4 (described in 72) and Schneider's *Drosophila* cell line 2 (ATCC Accession # CRL-1963) were compared based on their ability to (i) resist the cytopathic effects of Sindbis virus infection, (ii) produce high viral titers, (iii) support viral budding, and (iv) provide a superinfection block (see Table 2). While extensive cytotoxicity was observed in the case of C7-10 cells, Sindbis cytotoxicity to C6/36 and u4.4 cells was minimal to zero (Table 2). In contrast to C6/36 and u4.4 cells, C7-10 cells also did not provide a superinfection block. Of the two more efficient mosquito cell lines, C6/36 showed the highest peak titers and budding of virus was clear, where as u4.4 appeared not to support virus budding (Table 2). Various additional considerations, such as the extent of cell survival after transfection and the efficiency of transformant selection in the presence of antibiotics (blasticidin S, hygromycin B, and zeocin) further supported the superior properties of the *A. albopictus*-derived C6/36 cell line.

TABLE 2

Effect of Sindbis virus replication in various mosquito-derived cell lines.

| Cell line | % of virus positive cells following infection | Peak Titers | Cytotoxic effects | Budding | Evidence of vesicles containing virions fusing within cells | superinfection possible |
|---|---|---|---|---|---|---|
| C7-10 | 100 | 2.3 x 10⁹ | extensive and rapid in onset following infection | Yes | Yes | Yes |
| C6/36 | 100 | 2.3 x 10⁹ | Minimal | Yes | Yes | No |
| u4.4 | 100 | 3 x 10⁸ | None | No | Yes | No |

(Data compiled from references 38-44)

Example 2

Generation of C6/36-Derived Packaging Cell Line Producing Untargeted Recombinant Sindbis Vectors Interacting With High-Affinity Laminin Receptor Components Materials and Methods Vector Design. For generating the C6/36 packaging cell line, pIB/V5-His/DHBB construct was produced by cloning BamHI/XhoI 4415 bp-long Sindbis DHBB fragment encoding structural genes, capsid, E3, E2, 6K, and E1, into the BamHI/XhoI site of pIZ/V5-His vector (see FIG. 12 for the plasmid map). pIZ/V5-His vector carries a selectable marker for blasticidin S and is specifically designed to express gene sequences in insect cells (i.e., it contains the OpIE2 promoter [*Orgyia pseudotsugata* immediate early 2-promoter], which provides high-level constitutive expression of the gene of interest in insect cells). The 11169 bp-long AseI fragment encoding Sindbis replicase, β-galactosidase reporter gene and the subgenomic promoter was excised from the SinRep5/LacZ plasmid (Invitrogen), blunt-ended using T4DNA polymerase, and cloned into EcoRV site of another pIZ/V5 vector conferring zeocin resistance to transfected cells (see FIG. 13 for the plasmid map).

Generation of Packaging Cell Line. After a stable C6/36 clone had been generated with the pIZ/V5SinRep5-LacZ plasmid, it was transduced with the pIB/V5-His/DHBB and the cells subjected to double selection using both blasticidin S (50 mg/ml) and zeocin (600 mg/ml) as recommended by the supplier Invitrogen). To increase vector yield, packaging cells were released from the antibiotic selection pressure 48 hours to 1 week before production of virus batches.

Viral Titer Determinations. Baby hamster kidney cells encoding a reporter luciferase gene (BHK-LUC) that is activated only by Sindbis virus/vector infection (BHKSIN-LUC2, ATCC Accession No. 12071) were obtained from the American Type Culture Collection (Manassas, Va.) and maintained in minimum essential "alpha-modification media (alpha-MEM, JRH Bioscience, Lenexa, Kans.) supplemented with 5% fetal bovine serum (FBS, BRL-GIBCO Grand Island, N.Y.). Media was removed from the C6/36 cell culture and tested at various dilutions on BHKSINLUC2 cells (see FIG. 7).

Superinfection Assay. The C6/36 packaging cells infected with Sindbis vector and producing virus for approximately 12 months were compared to C6/36 cells that had never been infected with Sindbis or made to produce recombinant Sindbis virus by transfection of the Sindbis-derived vector plasmids (see FIG. 8).

Results

A novel efficient recombinant Sindbis vector packaging cell line was generated by transducing C6/36 mosquito cells with the pIZ/V5SinRep5-LacZ and pIB/V5-His/DHBB plasmids. The vector pIB/V5-His/DHBB comprises conventional Sindbis structural genes (including E1 and E2 envelope genes responsible for the recognition of a 67 kDa high-affinity laminin receptor on the cell surface), while pIZ/V5SinRep5-LacZ encodes the Sindbis replicon and the desired gene (β-galactosidase) to be transfected (see FIGS. 3, 4, 12, and 13). The DHBB helper strand is packaging signal negative so that its genome is not incorporated into the vectors produced, thereby rendering the progeny vectors replication incompetent.

Figure 6:
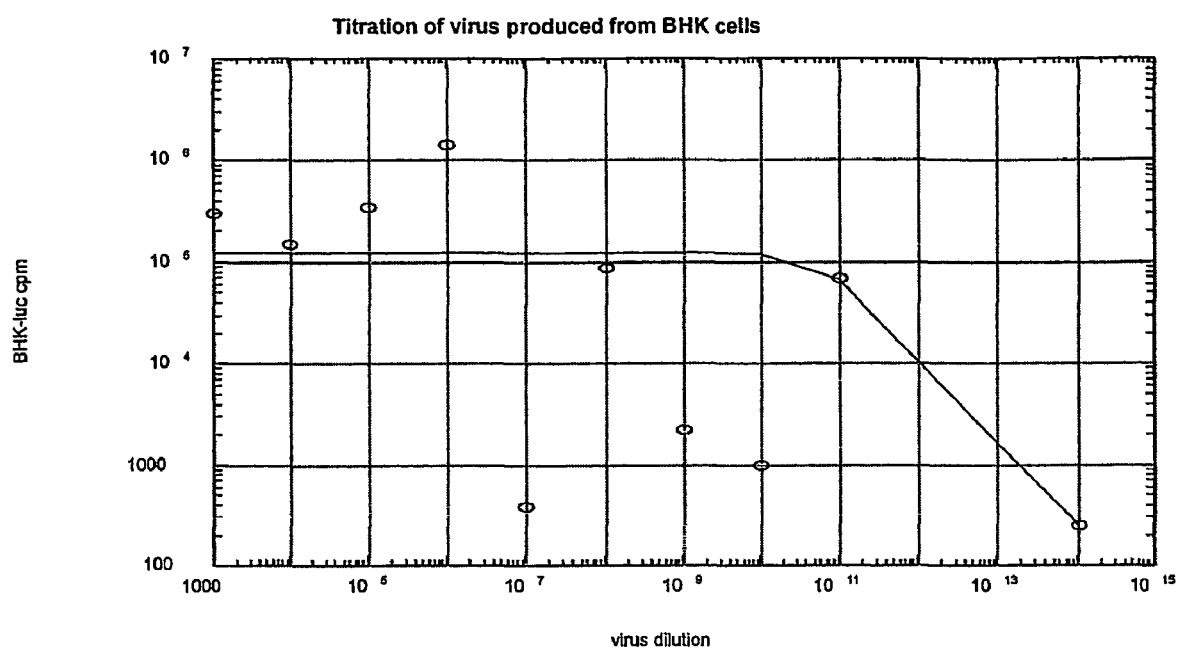
FIG. 6. Typical titers of Sindbis vectors produced from BHK cells by the standard procedure involving in vitro RNA production and electroporation.
Figure 7:
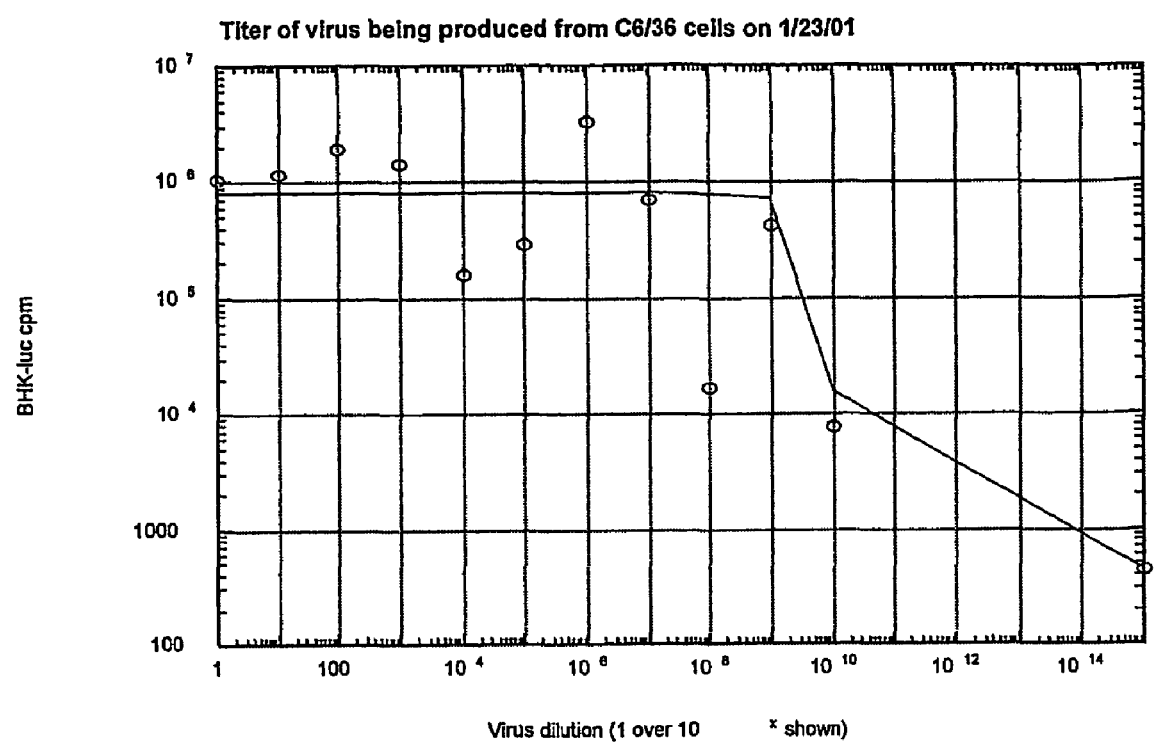
FIG. 7. Titers of virus produced from transfected C6/36 cells assayed using BHK cells encoding a reporter luciferase gene (BHK-luc cells).

Titers of recombinant virus produced from transfected C6/36 cells were tested using BHK cells encoding a reporter luciferase gene (BHKSINLUC2) that is activated only by Sindbis virus/vector infection (FIG. 7). As compared to typical titers of Sindbis vectors produced from BHK cells by the standard procedure involving in vitro RNA production and electroporation (shown in FIG. 6), titers of virus produced from transfected C6/36 insect cells appeared to be similar.

Figure 8:
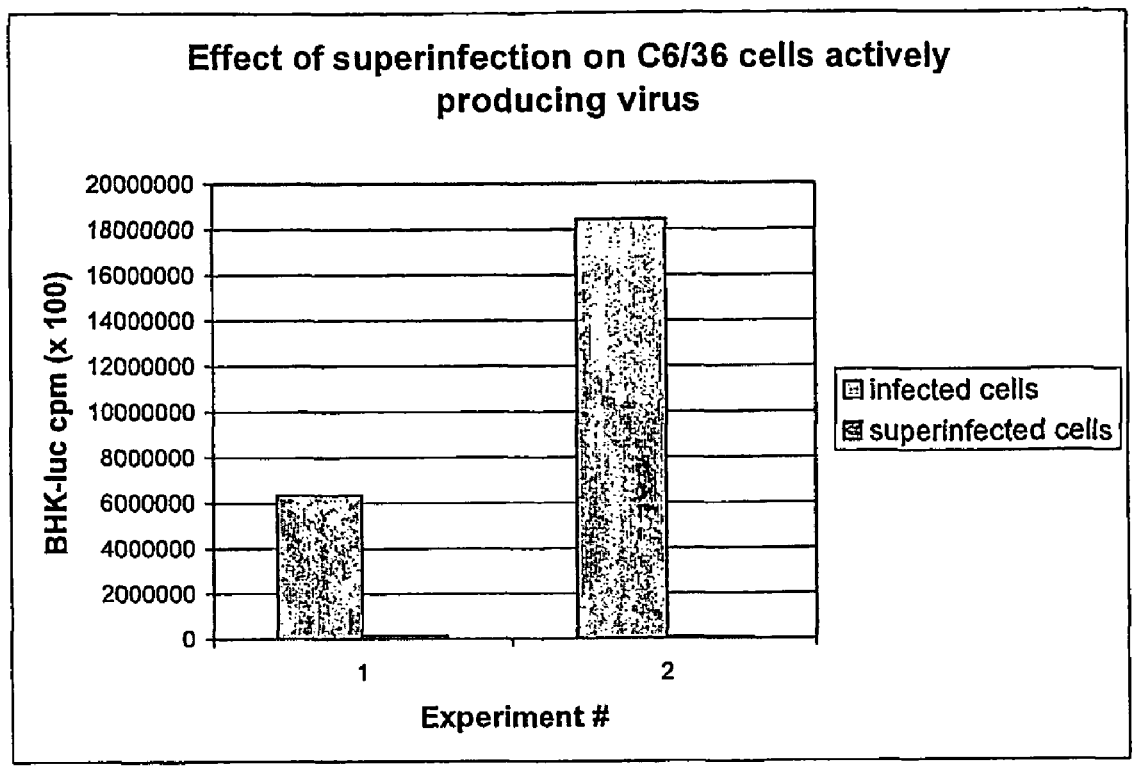
FIG. 8. Assay of the ability of the established viral infection to interfere with superinfection by the same virus (homologous interference). Packaging insect cells producing virus for approximately 12 months are compared to C6/36 cells that had never been infected with Sindbis virus or transfected with Sindbis-derived recombinant vectors.

Riedel and Brown (71) have shown that *A. albopinctus* cells persistently infected with Sindbis virus released into the surrounding medium an antiviral agent, which inhibits Sindbis production in cultured insect cells. To investigate this issue further, the ability of the established viral infection to interfere with superinfection by the same virus (homologous interference) was examined by comparing the packaging insect cells producing recombinant virus for approximately 12 months to C6/36 cells that had never been infected with Sindbis or made to produce Sindbis virus by transfection of the Sindbis-derived vector plasmids. As shown in FIG. 8, a dramatic difference (ranging between about 100-fold and about 500,000-fold) was observed between the effects of Sindbis infection on naïve C6/36 cells and the packaging C6/36 cultures.

Discussion

The ability to produce recombinant Sindbis vectors from continuous cultures has been greatly hindered by the apoptosis-inducing potential of this virus in mammalian cells. Thus, the approach currently in use, which involves in vitro transcription of Sindbis plasmids to produce vector RNA followed by electroporation of BHK cells, allows vector harvesting from culture supernatant for only one or two days. Clearly, this approach is labor intensive, costly and impractical for large-scale use.

In an effort to overcome these limitations, insect cells, in particular the C6/36 mosquito cell line, have been used for recombinant Sindbis vector production. These cells are substantially resistant to the apoptosis-induced properties of Sindbis vectors and can be engineered to establish long-term vector producing cultures, in which acceptable virus titers (greater than $10^6$ per ml) can be produced for extended periods of time (more than 2 weeks and preferably over 1 year).

Specifically, disclosed herein is the methodology used to develop a permanent mosquito C6/36 packaging cell line that can produce replication defective Sindbis vectors at persistently high titers (greater than $10^6$ per ml, see FIG. 7) without any associated cytopathology. A specific recombinant Sindbis virus-derived vector produced by the packaging cells of the present invention encodes the β-galactosidase gene and targets cells expressing the high-affinity laminin receptor. Accordingly, this vector can be used for gene delivery to a large number of cell types (57, 58, 67). In particular, as previously demonstrated, this vector can be used for gene delivery to various tumor cells which express high levels of high-affinity laminin receptors (45-55, 59-67).

Example 3

Comparison of the In Vivo Efficacy of Recombinant Sindbis Vector Preparations Produced by Mammalian and Mosquito Cell Lines Materials and Methods Cell lines and plasmids. A Sindbis vector-producing C6/36 packaging cell line was generated and used as described in Example 2, above. Baby hamster kidney (BHK-21, ATCC Accession No. CCL-10) cells were obtained from the American Type Culture Collection (Manassas, Va.) and maintained in minimum essential media (Alpha-MEM, JRH Bioscience, Lenexa, Kans.) supplemented with 5% fetal bovine serum (FBS, BRL-GIBCO, Grand Island, N.Y.).

FIGS. 1-5 show-schematic representation of the Sindbis virus-derived expression and helper vectors. A Sindbis virus-based expression vector SinRep/LacZ (Bredenbeek et al., J Virol, 1993, 67: 6439-6446, Invitrogen Co.) contains the packaging signal, nsp1-4 for replicating the RNA transcript, the promoter for subgenomic transcription, and the LacZ gene. A helper plasmid DH-BB which contains the structural genes, capsid, E3, E2, 6K, and E1, (Bredenbeek et al., 1993, supra, Invitrogen Co.) is necessary for viral packaging.

In vitro transcription and transfection for Sindbis virus production in BHK cells. Plasmids for in vitro transcription were prepared with the QIAGEN plasmid kit (Chatsworth, Calif.). A helper plasmid DH-BB and an expression plasmid SinRep/LacZ were linearized by XhoI restriction enzyme digestion and purified by phenol/chloroform extraction followed by ethanol precipitation. Transcription reactions, from the SP6 promoter, were carried out by using the InvitroScript Cap Kit (Invitrogen Co.) to produce large quantities of capped mRNA transcripts. The quality of RNA was checked on agarose gels. For cotransfection of helper DH-BB and SinRep/LacZ into BHK cells, electroporations were performed as described before (Ohno et al., Nature Biotechnol., 1997, 15: 763-767). Electroporated cells were transferred to 10 ml of Alpha-MEM containing 5% FCS and incubated for 12 hrs. Cells were then washed with phosphate-buffered saline (PBS) and incubated in 10 ml of Opti-MEM I medium (GIBCO-BRL) without FCS. After 24 hr, culture supernatants were harvested and aliquots were stored at −80° C.

Infection Assay. Infectivity of Sindbis virus produced by both BHK and C6/36 cells on BHK cell line was determined by transfer of the Sindbis virus vector and measurement of β-galactosidase activity. Viral supernatant dilutions (250 µl) were added to $2\times10^5$ cells in 12-well plates and after 1 hr incubation at room temperature, cells were washed with PBS and incubated with medium for 24 hrs. Viral infection was evaluated by X-gal staining: infected cells were fixed in PBS containing 0.5% glutaraldehyde for 20 min followed by washing with PBS three times; cells were stained with PBS containing 1 mg/ml X-gal (5-Bromo-4-chloro-β-D-galactropyranoside, Fisher Scientific), 5 mM potassium ferricyanide, 5 mM potassium ferrocyanide, and 1 mM $MgSO_4$ at 37° C. for 3 hr. Titers were expressed as LacZ CFU per milliliter (CFU is defined in terms of cells staining blue by X-gal).

Animal model and in vivo transfection. All severe combined immunodeficient (SCID) mice used were obtained from Taconic (Germantown, N.Y.) and were 6-8 weeks old at the time experiments were begun. BHK cells were grown as subcutaneous tumors from an initial inoculom of approximately $10^7$ cells. Eight weeks after tumor injection, mice were injected with 250 µl of Sindbis virus vector (DH-BB) once or on three consecutive days via the intraperitoneal route (i.p.). Control mice were injected with Opti-MEM I medium using the same procedure. All mice were sacrificed the next day after final transfection.

β-Gal immunostaining. Immunohistochemical detection of β-galactosidase was performed on formalin fixed paraffin embedded tissues with appropriate positive (transfected cell lines with β-galactosidase vector) and negative controls on an automated immunostainer, NexES (Ventana Medical Systems, Tucson, Ariz.) by a standard streptavidin-biotin horseradish peroxidase complex detection using 3,3-diaminobenzidine (DAB) as a chromagen. Briefly, transfected cell lines were grown under appropriate growth conditions to a cell density of approximately $10^6$ cells/ml. These cells were gently pelleted and resuspended in a small amount of media Equal proportions of fibrin and thrombin were added to this suspension to create a fibrin/thrombin/cell clot that was fixed in 10% neutral buffered formalin. Tumor samples were excised from the animals and fixed in 10% neutral buffered formalin. Both the cell clot and the tissues were fixed for 12 hours in formalin and processed for paraffin embedding. 5 µm thick tissues sections were prepared onto electrostatically charged glass slides, and baked at 60° C. overnight. The slides were deparaffinized by three washes in xylene followed by rehydration through graded alcohols (100%, 90%, and 70%). One slide was stained with hematoxylin and eosin while the others were used for the β-galactosidase detection with anti-β-galactosidase mouse monoclonal antibody (BIODESIGN, Kennebunk, Me.), which was used at a dilution of 1:50 with overnight incubation. Cellular localization of β-galactosidase was cytoplasmic.

β-Gal assay. The expression of β-gal protein in the tissue was investigated by β-gal assay reagent kit (PIERCE, Rockford, Ill.). The tissues were homogenized, in 3 ml of PBS, with a glass Pyrex homogenizer using a type B pestle (30 strokes). Homogenized samples were centrifuged at 2500 rpm at 4° C. for 10 minutes. The supernatant was harvested and the pellet fraction was resuspended with 2 ml of PBS and aliquots were harvested as tissue components. 50 µl of each aliquot were mixed with 50 µl of All-in One™ β-Gal Assay Reagent (PIERCE, Rockford, Ill.) and transferred to a 96 well plate. After incubation at 37° C. for 30 min, absorbence at 405 nm was read using a spectrophotometer. Each protein concentration was determined by BIORAD reagent (BIORAD) and the result was adjusted per 100 mg protein.

Results and Discussion

The high affinity laminin receptor (HALR) is the ligand through which Sindbis virus normally infects most cells (58-59, 67). As fully described in co-owned, copending U.S. patent application Ser. No.60/279,051, filed Mar. 27, 2001, Sindbis vectors with natural HALR affinity preferentially infect and kill tumor cells in vivo. This preferential infection is thought to reflect much higher levels of high-affinity laminin receptors on tumor cells compared to normal cells (45-55, 59-67). Thus, it is disclosed in the co-pending U.S. patent application that after infection of SCID mice containing rapidly growing BHK-derived tumors, the expression of the reporter β-galactosidase protein was apparent in the BHK tumor cells, yet no significant expression was observed in normal tissues examined. Importantly, viral entry and expression of viral genes was accompanied by a high degree of tumor necrosis leading to a complete tumor regression.

Figure 9:
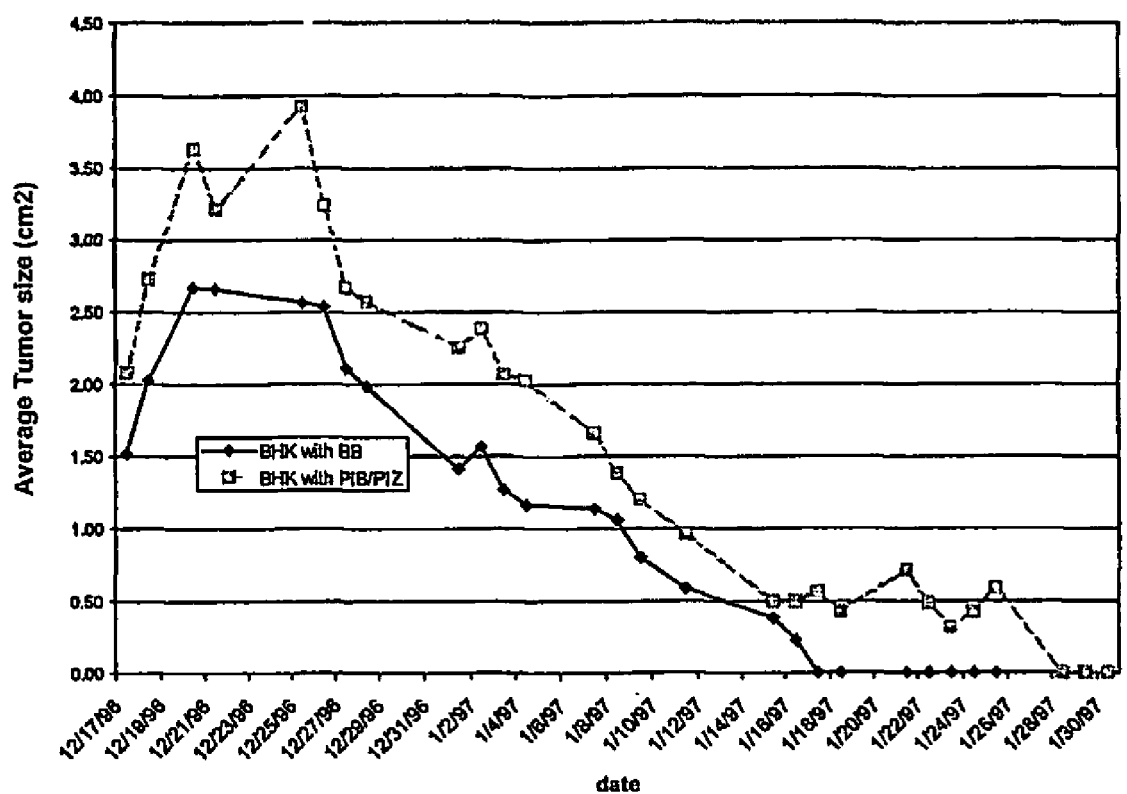
FIG. 9. Comparison of the in vivo efficacy of BHK- and C6/36-derived viral preparations as a function of their ability to induce elimination of rapidly growing BHK tumors in SCID mice.

To compare further the recombinant Sindbis vectors produced in a novel C6/36 packaging cell line of the present invention (see Example 2, above) with the vector obtained from electroporating BHK cells with in vitro synthesized RNAs, the efficacy of the two preparations was measured by their ability to induce a complete tumor regression in SCID mice growing BHK tumor cells. Results of this experiment (shown in FIG. 9) indicate that viral activity obtained from the insect packaging cell line is sufficient to achieve tumor regression efficacy in animals.

Example 4

Methods for Increasing Titers of Recombinant Sindbis Vectors Produced by Packaging Cell Lines Centrifugation. Sindbis vectors were produced using BHK cells as described above. 7.5 ml of the virus was placed in an ultracentrifuge tube and centrifuged using a Ti-70 fixed angle rotor. Centrifugation was performed at 4° C. for 1 hour in a L7-55 Beckman centrifuge. After centrifugation the supernatant was removed and the viral pellet was resuspended in 350 µl of Opti-MEM I medium.

Titer determination was done using BHK cells as follows. The BHK cells were plated into a 12-well plate and allowed to adhere overnight. The next day the virus was diluted serially at 1/10 dilutions until the final dilution of $10^{-11}$. As a control, Sindbis vector that was not concentrated was titered as well. All dilutions of virus were made using Opti-MEM I medium. After all dilutions were made, 500 µl of each dilution was used to infect the plated BHK cells.

Infection was performed by layering 500 µl over the BHK cells in which the media had been removed and incubating with shaking for 1 hour at room temperature. After the 1-hour incubation the virus was removed and the wells were washed once with PBS. The PBS was removed and normal growth media was added. The plates were placed in the 37° C. $CO_2$ incubator overnight. The next day the cells were assayed for β-galactosidase activity using the standard X-gal staining method. Blue cells were counted and the titer was determined.

Figure 10:
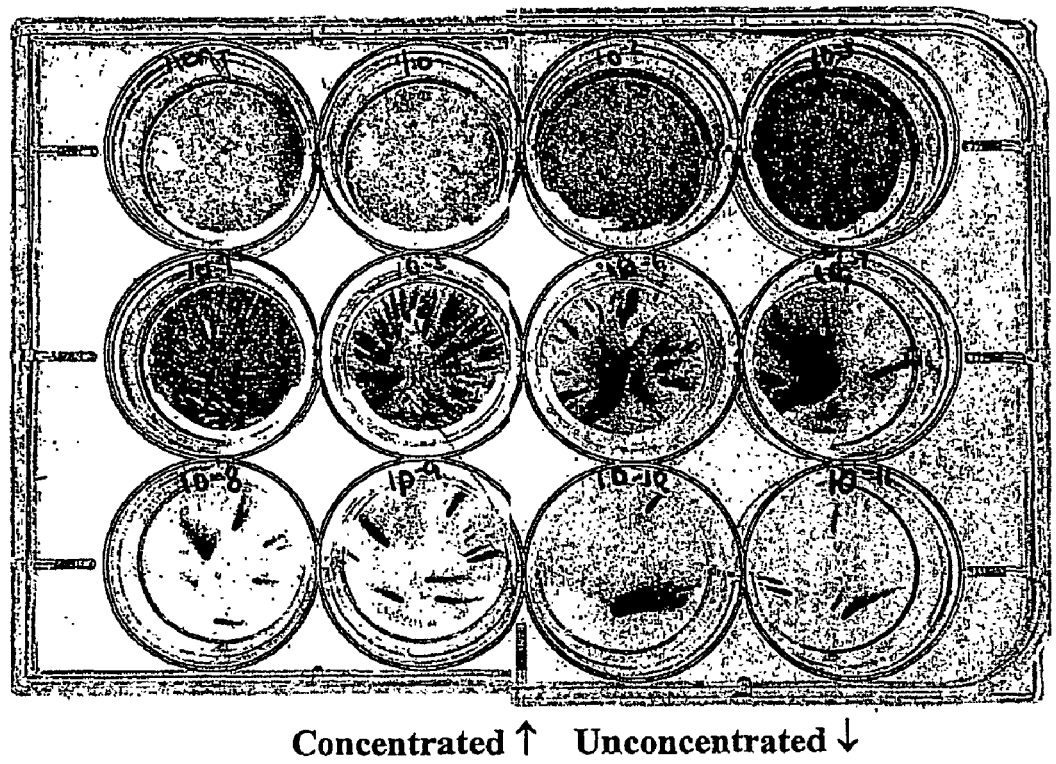
FIG. 10. Determination of titer and infectivity of the centrifugation-concentrated recombinant Sindbis vector using BHK cells.
Figure 10:
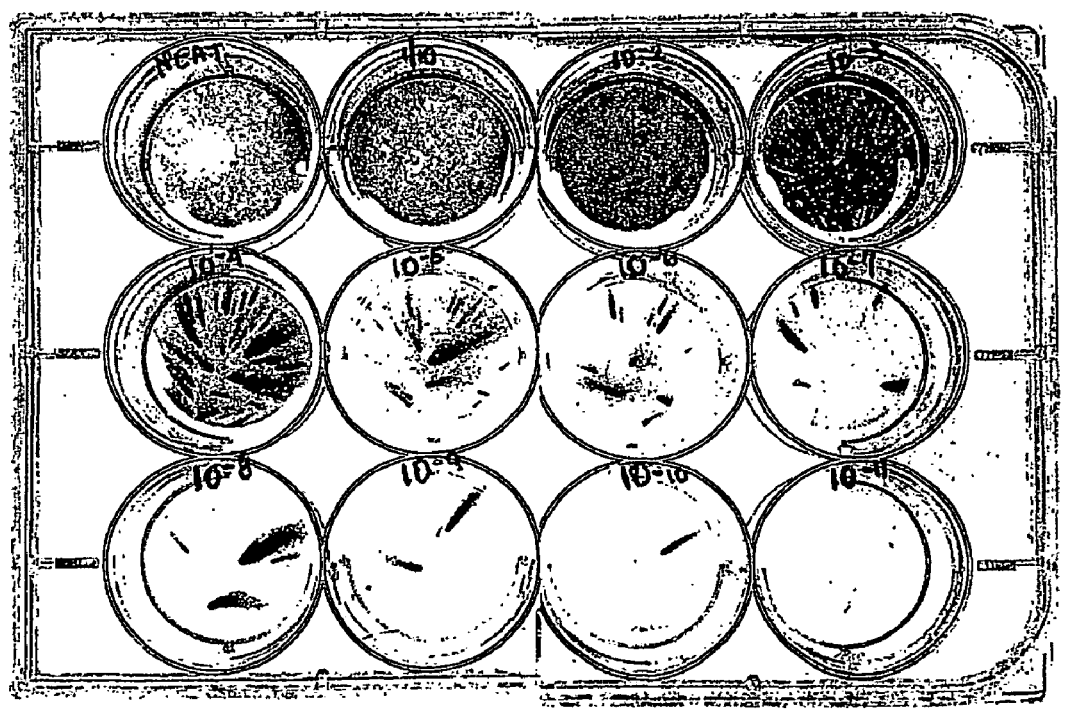
Figure 11:
FIG. 11. Heterokaryons of C6/36 insect cells and BHK cells infected with a Sindbis vector carrying the β-galactosidase gene (left) and uninfected (right). These heterokaryons resist apoptosis-mediated by Sindbis infection and survive for at least 4 weeks after infection. A higher magnification of the uninfected heterokaryon is provided to facilitate seeing details (the dark blue staining of the infected cells makes it more difficult to distinguish the nuclei from the rest of the cell).
Figure 11:
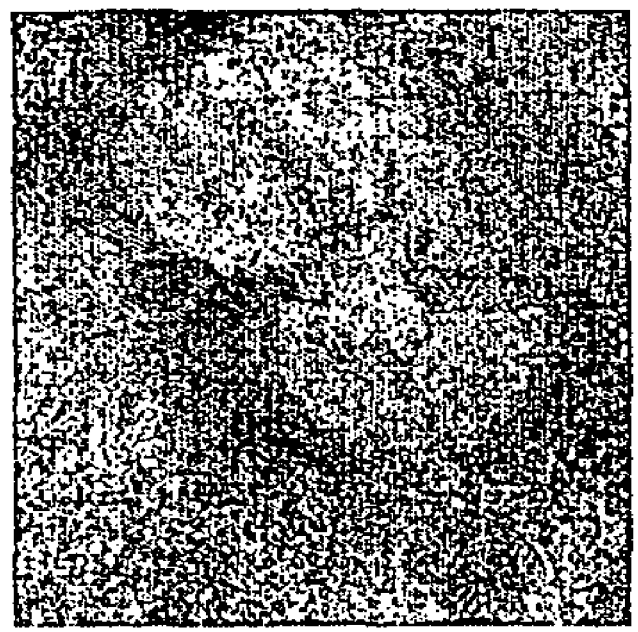
Figure 12:
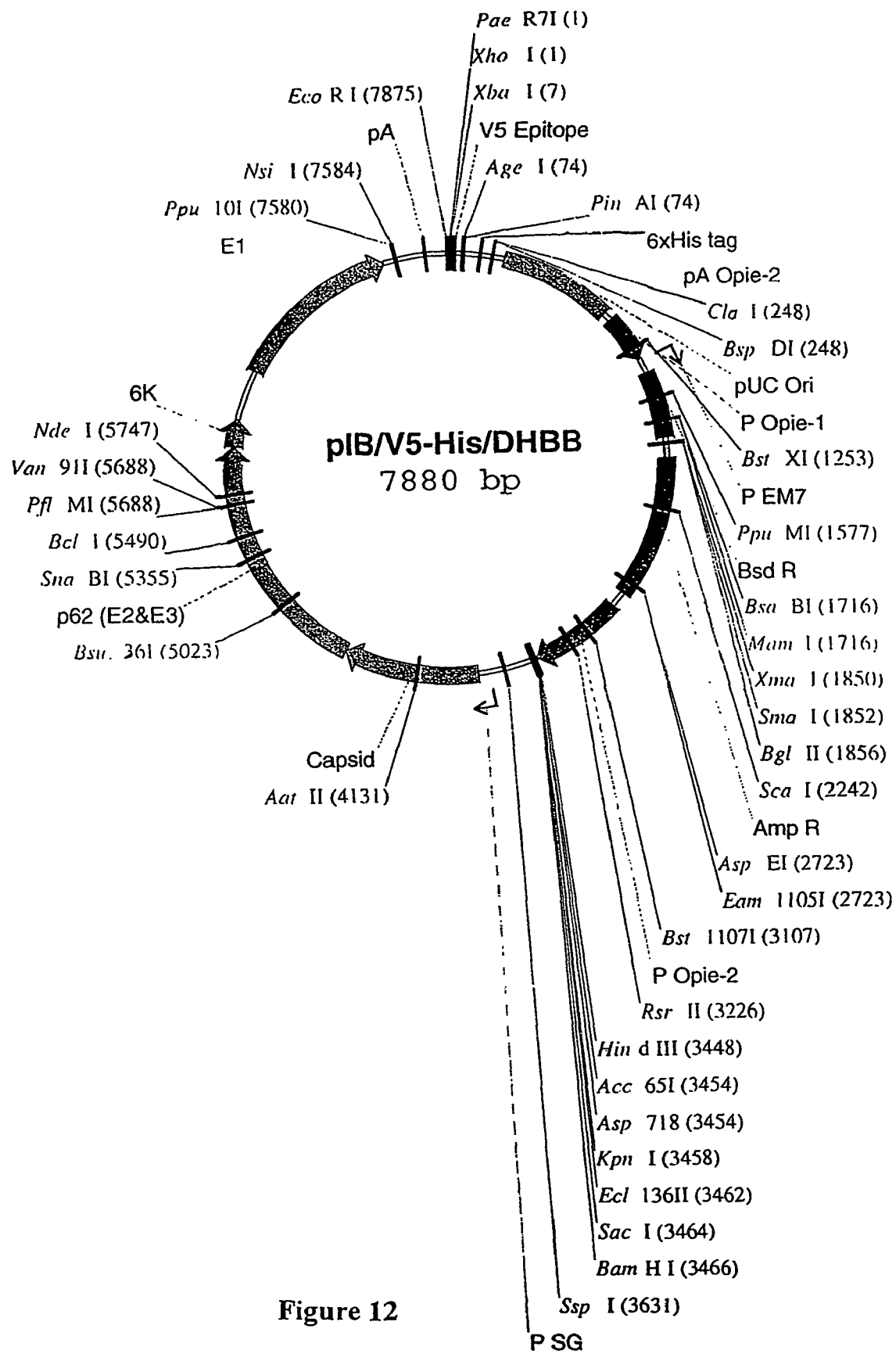
FIG. 12. Plasmid map of pIB/V5-His/DHBB.
Figure 13:
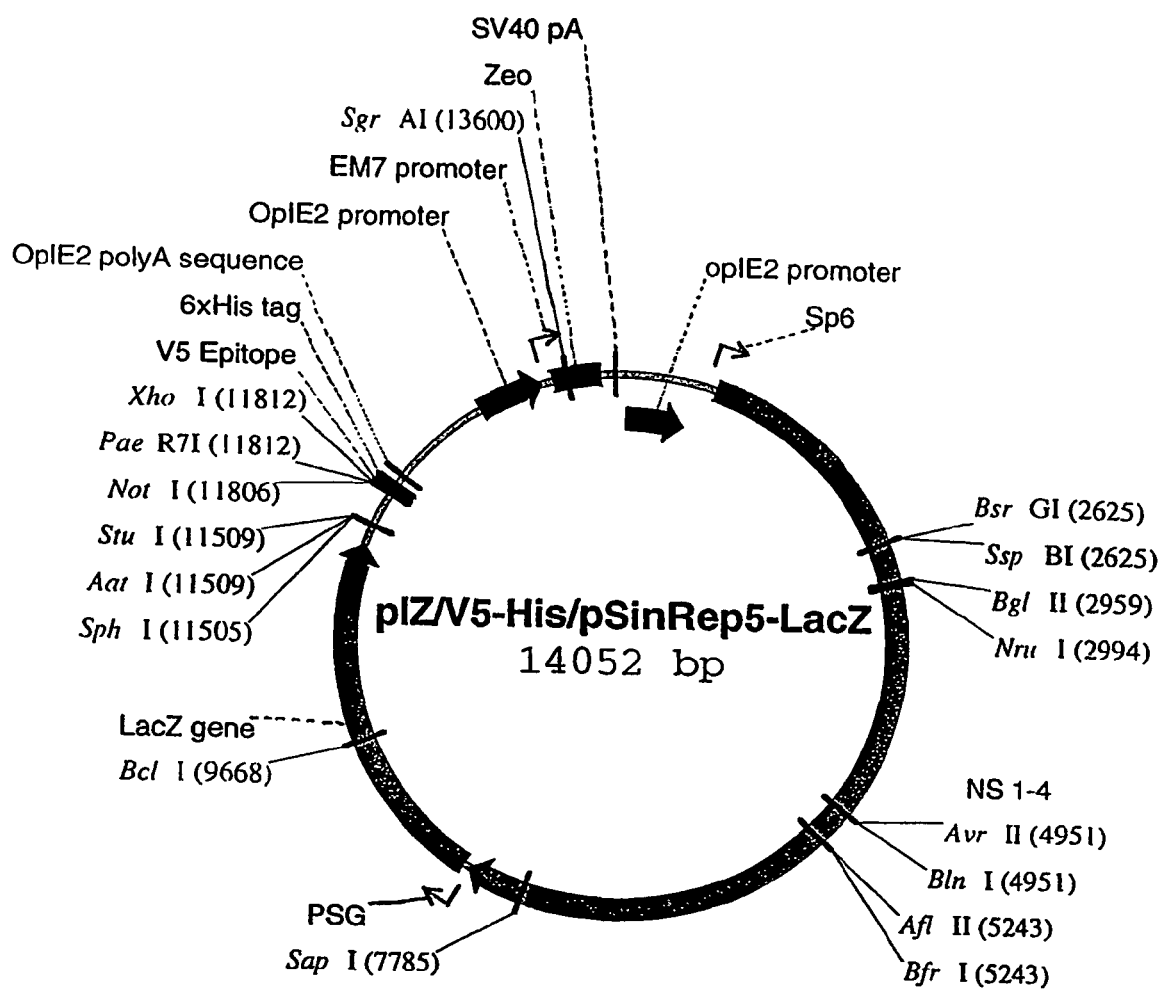
FIG. 13. Plasmid map of pIZ/V5SinRep5-LacZ.
Figure 14:
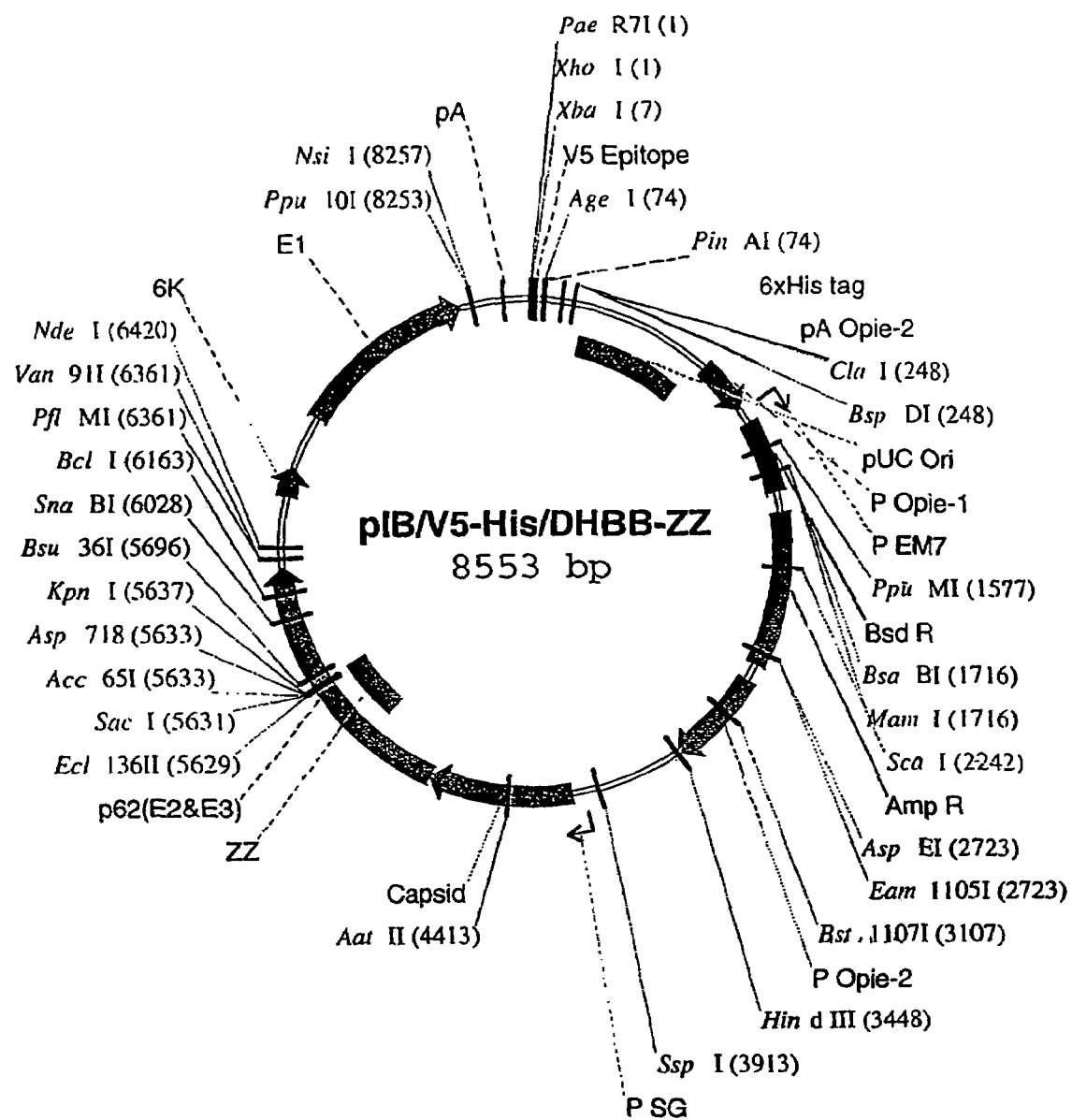
FIG. 14. Plasmid map of pIB/V5-His/DHBB-ZZ.
Figure 15:
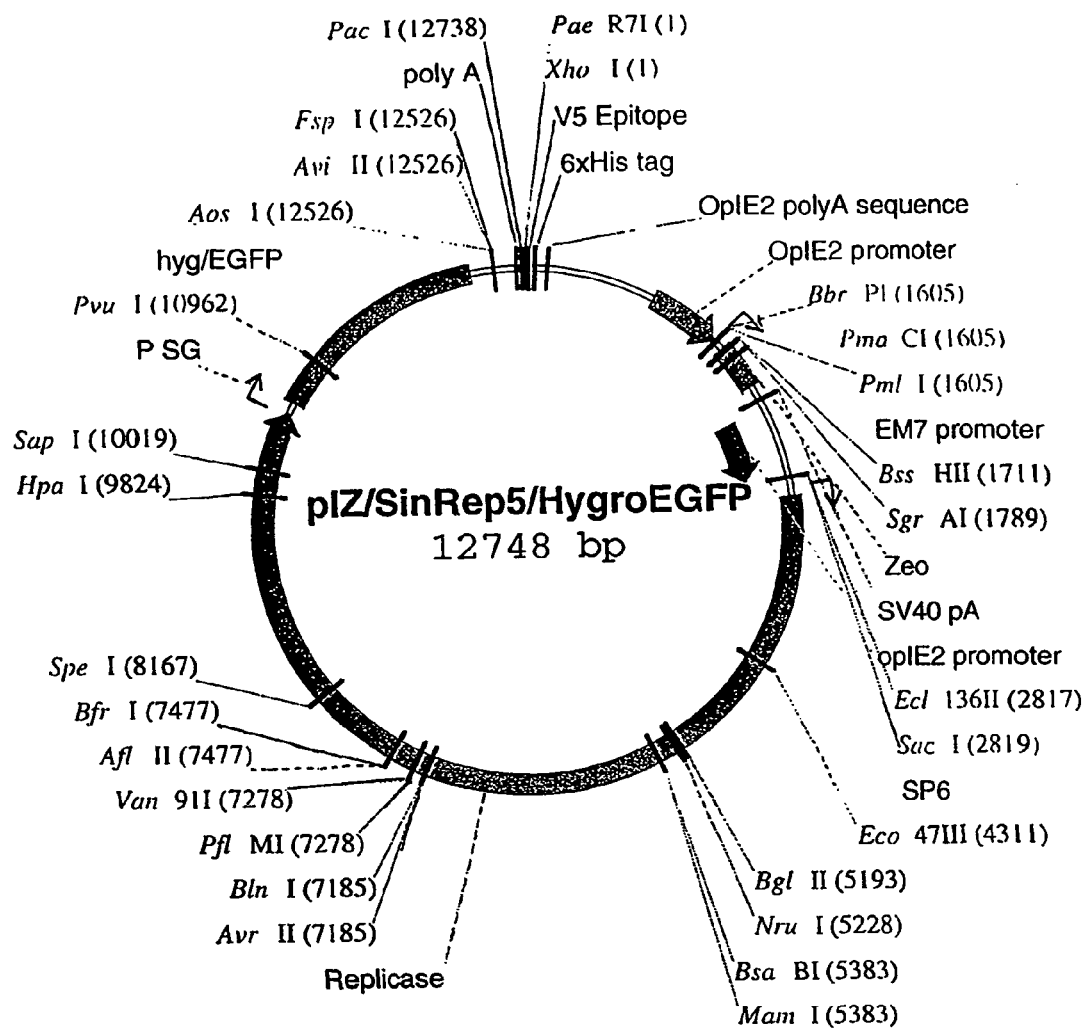
FIG. 15. Plasmid map of pIZ/V5SinRep5-HygroEGFP.

The degree of concentration achieved, as illustrated in the accompanying photographs of the plates (FIG. 10), indicates that an approximately 20-fold increase in concentration was achieved demonstrating that the ultracentrifugation procedure leads to efficient Sindbis vector concentration without the loss of infectivity.

Lyophilization. Sindbis vector was generated as previously described (35). 7.5 ml of virus was cold lyophilized overnight using standard methods of lyophilization (74-76). The lyophilized material was then resuspended in 350 µl of Opti-MEM I medium. Titer determination was done as above. Similar results were obtained.

Bioreactors. HygroEGFP-Sindbis vector-producing cell cultures are grown in bioreactors to permit cells to be maintained at much higher densities (approximately $2 \times 10^6$ prior to expansion in bioreaction). Cells containing HygroEGFP-encoding constructs are sorted and enriched in culture by detecting the expression of the green fluorescent protein using a FAC Scan (Becton Dickinson Immunocytometry System, Mountainview, Calif.).

All experimental strategies presented above lead to an additional 10 to 100-fold increase in the virus/vector titer after its production in the packaging cell line of the present invention.

Example 5

Generation of C6/36-Derived Packaging Cell Line Producing Targeted Recombinant Sindbis Vectors Interacting With Specific Surface Antigens Using the same methodology as disclosed in Example 2, above, the present inventors have constructed a C6/36-derived packaging cell line producing a recombinant Sindbis vector that targets cells on the basis of Protein A-antibody-cell surface antigen expression. The Protein A-IgG, targetable vector of the present invention contains the Protein A modified helper strand DHBBZZ (4715 bp-long HindIII/XhoI fragment) cloned into HindIII/XhoI site of pIZ/V5 vector conferring zeocin resistance (see FIGS. 4 and 14). The Sindbis replicase and the subgenomic promoter were excised from the SinRep5/LacZ plasmid (Invitrogen) and cloned together with Hygromycin-EGFP reporter gene in another pIZ/V5 vector conferring hygromycin resistance to transfected cells (see FIGS. 3 and 15). The hygromycin-EGFP fusion gene was used as an additional selectable marker. Cells expressing the highest amount of EGFP were selected using a Fluorescence Activated Cell Sorter (FACS) described above.

An insect vector containing the Sindbis replicase and subgenomic promoter along with a hygromycin-EGFP fusion reporter gene was constructed. This vector confers hygromycin resistance to transfected cells and the hygro-EGFP fusion gene provides an additional selectable marker.

The vector was constructed by first cloning a 9924 bp MluI/STUI fragment of pSinRep5 (Invitrogen) into the MluI/SmaI sites of the pItygroEGFP vector (Clonetech) to create pSinRep5/HygroEGFP. A SacI/XhoI, 9930 bp, fragment from pSinRep5/HygroEGFP was then cloned into the SacI/XhoI sites of pIZ/V5 to create pIZ/SinRep5/HygroEGFP.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

References

1. Di Ianni M, Di Florio S, Venditti G, Falzetti F, Mannoni P, Martelli M F, Tabilio A. T lymphocyte transduction with herpes simplex virus-thymidine kinase (HSV-tk) gene: comparison of four different infection protocols. J Hematother Stem Cell Res 8:645-652, 1999.
2. Morling F J, Russell S J Enhanced transduction efficiency of retroviral vectors coprecipitated with calcium phosphate. Gene Ther 2:504-508, 1995.
3. Lam J S, Reeves M E, Cowherd R, Rosenberg S A, Hwu P Improved gene transfer into human lymphocytes using retroviruses with the gibbon ape leukemia virus envelope. Hum Gene Ther 7:1415-1422, 1996.
4. Kume A, Hashiyama M, Suda T, Ozawa K Green fluorescent protein as a selectable marker of retrovirally transduced hematopoietic progenitors. Stem Cells 17:226-232, 1999.
5. Thompson, L. Monkey Tests Spark Safety review. Science 257: 1854,1992.
6. Miyao Y, Ikenaka K, Kishima H, Tamura M, Nakamura K, Kurumi M, Hayakawa T, Shimizu K FUT-175, a synthetic inhibitor of the complement pathway, protects against the inactivation of infectious retroviruses by human serum. Hum Gene Ther 8:1575-1583, 1997.
7. Russell D W, Berger M S, Miller A D. The effects of human serum and cerebrospinal fluid on retroviral vectors and packaging cell lines. Hum Gene Ther 6:635-641, 1995.
8. Rother R P, Fodor W L, Springhorn J P, Birks C W, Setter E, Sandrin M S, Squinto S P, Rollins S A. A novel mechanism of retrovirus inactivation in human serum mediated by anti-alpha-galactosyl natural antibody. J Exp Med 182:1345-55, 1995.
9. Ginsberg, H. S. The ups and downs of adenovirus vectors. Bulletin of the New York Acad. Med. 73:53-58, 1996.
10. Sparer, T. E., Wynn S. G., Clark, D. J., Kaplan, J. M., Cardoza, L. M., Wadsworth, S. C., Smith, A. E., and Gooding, L. R. Generation of cytotoxic T lymphocytes against immunoreactive epitopes after multiple immunizations with adenovirus vectors is dependent on haplotype. J. Virol. 71:2277-2284, 1997.
11. Duncan S J, Gordon F C, Gregory D W, McPhie J L, Postlethwaite R, White R Willcox H N. Infection of mouse liver by human adenovirus type 5. J Gen Virol. 40:45-61, 1978.
12. Alemany R, Suzuki K, Curiel D T. Blood clearance rates of adenovirus type 5 in mice. J Gen Virol. 81 Pt 11:2605-2609, 2000.

13. Alemany R, Balague C, Curiel D T. Replicative adenoviruses for cancer therapy. Nat Biotechnol. 18:723-727, 2000.
14. Taylor, R M and H S Hurlbut (1953). "Isolation of coxsackie-like viruses from mosquitoes." J. Egypt. Med. Assoc. 36: 489-494.
15. Taylor, R M, H S Hurlbut, T H Work, J R Kingsbury and T E Frothingham (1955). "Sindbis virus: A newly recognized arthropod-transmitted virus." Am. J. Trop. Med. Hyg. 4: 844-846.
16. Shah, K. V, H. N. Johnson, T. R. Rao, P. K. Rajagopalan, and B. S. Lamba. Isolation of five strains of Sindbis virus in India. Ind. J. Med. Res 48:300-308, 1960.
17. Straus J H and Straus E G. The alphaviruses: gene expression, replication, and evolution. Microbiol. Rev. 58: 491-562, 1994.
18. Altman-Hamamdzic, S, Groseclose C, Ma J-X, Hamamdzic D, Vrindavanam N S, Middaugh L D, Parratto N P and Sallee F R. Expression of β-galactosidase in mouse brain: utilization of a novel nonreplicative Sindbis virus vector as a neuronal gene delivery system. Gene Ther. 4; 815-822, 1997
19. Gwag B J, Kim E Y, Ryu B R, Won S J, Ko H W, Oh Y J, Cho Y G, Ha S J, and Sung Y C. A neuron-specific gene transfer by a recombinant defective Sindbis virus. Mole. Brain Research. 63: 53-61,1998.
20. Bredenbeek P J, Frolov I, Rice C M and Schlesinger S. Sindbis virus expression vectors: Packaging of RNA replicons by using defective helper RNAs. J Virol, 67; 6439-6446, 1993
21. Liljestrom P and Garoff H. A new generation of animal cell expression vectors based on the Semiliki Forest virus replicon. Biotechnology 9: 1356-1361. 1991.
22. Piper R. C.,Slot J W, Li G, Stahl P D, James D E. Recombinant Sindbis virus as an expression system for cell biology. *Meth. Cell Biol*. 43:55-78, 1994.
23. Grusby M J, Auchincloss H Jr., Lee R, Johnson R S, Spencer J P, Zijlstra M, Jaenisch R, Papaioannou V E, Glimcher L H. Mice lacking major histocompatibility complex class I and class II molecules. Proc Natl. Acad. Sci U S A. 90:3913-3917, 1993.
24. Tsuji M, Bergmann C C, Takita-Sonoda Y, Murata K, Rodrigues E G, Nussenzweig R S, Zavala F. Recombinant Sindbis viruses expressing a cytotoxic T-lymphocyte epitope of a malaria parasite or of influenza virus elicit protection against the corresponding pathogen in mice. J Virol 72:6907-6910, 1998.
25. Hariharan M J, Driver D A, Townsend K, Brumm D, Polo J M, Belli B A, Catton D J, Hsu D, Mittelstaedt D, McCormack J E, Karavodin L, Dubensky T W Jr., Chang S M, Banks T A. DNA immunization against herpes simplex virus: enhanced efficacy using a Sindbis virus-based vector. J Virol 72:950-958, 1998.
26. Pugachev K V, Mason P W, Shope R E, Frey T K. Double-subgenomic Sindbis virus recombinants expressing immunogenic proteins of Japanese encephalitis virus induce significant protection in mice against lethal JEV infection. Virology 212:587-594, 1995.
27. Xiong C, Levis R, Shen P, Schlesinger S, Rice CM and Huang H V. Sindbis virus: an efficient, broad host range vector for gene expression in animal cells. Science 243: 1188-1191, 1989.
28. Levine B, Huang Q, Issacs J T, Reed J C and Hardwick J M. Conversion of lytic to persistent alphavirus infection by the bcl-2 cellular oncogene. Nature 361; 739-742, 1993
29. Jan J T and Griffin D E. Induction of apoptosis by Sindbis virus occurs at cell entry and does not require virus replication J Virol. 73; 10296-10302, 1999
30. Jan J T, Chatterjee S and Griffin D E. Sindbis virus entry into cells triggers apoptosis by activating sphingomyelinase, leading to the release of ceramide. J Virol. 74: 6425-6432, 2000.
31. Balachandran S., Roberts P C, Kipperman T, Bhalla K N, Compans R W, Archer D R and Barber G N. Alpha/Beta interferons potentiate virus-induced apoptosis through activation of the FADD/Caspase-8 death signaling pathway. J. Virol. 74:1513-1523, 2000.
32. The Subcommittee on Arbovirus Laboratory Safety of the American Committee on Arthropod-Borne Viruses. Laboratory safety for arboviruses and certain other viruses of vertebrates. Am. J. Trop. Med. Hyg 29:1359-1381, 1980.
33. Turrell, M J. Horizontal and vertical transmission of viruses by insect and tick vectors, p127-152. In T. P. Monath (ed.), The arboviruses: epidemiology and ecology. CRC Press, Inc. Boca Raton, Fla., 1988.
34. McGill P E Viral infections: alpha-viral arthropathy. Baillieres Clinical Rheumatology 9:145-150, 1995.
35. Ohno K, Sawai K, Iijima Y, Levin B and Meruelo D. Cell-specific targeting of Sindbis virus vectors displaying IgG-binding domain of protein. Nature (Biotechnol.) 15: 763-767, 1997.
36. Agapov, E. V., Frolov, I., Lindenbach, B. D., Pragai, B. M., Schelesinger, S., and Rice, C. M. Noncytopathic Sindbis virus RNA vectors for heterologous gene expression. Proc. Natl. Acad. Sci. 95:12989-12994, 1998.
37. Polo J M, Belli B A, Driver D A, Frolov I, Sherrill S, Hariharan M J, Townsend K, Perri S, Mento S J, Jolly D J, Chang S M, Schlesinger S, and Dubensky T W Jr. Stable alphavirus packaging cell lines for Sindbis virus and Semliki Forest virus-derived vectors. Proc Natl Acad Sci USA. 96:4598-4603, 1999.
38. Karpf A R, Brown D T. Comparison of Sindbis virus-induced pathology in mosquito and vertebrate cell cultures. Virology. 240:193-201, 1998.
39. Karpf. A R, E Lenches, E G Strauss, J H Strauss and D T Brown. Superinfection Exclusion of Alphaviruses in Three Mosquito cell lines Persistently infected with Sindbis Virus. J. Virol. 71:7119-7123, 1997
40. Karpf A R, Blake J M, Brown D T. Characterization of the infection of Aedes albopictus cell clones by Sindbis virus. Virus Res. 1997 July;50(1):1-13
41. Luo T, Brown D T. Purification and characterization of a Sindbis virus-induced peptide which stimulates its own production and blocks virus RNA synthesis. Virology. 194:44-49, 1993.
42. Miller M L, Brown D T. Morphogenesis of Sindbis virus in three subclones of Aedes albopictus (mosquito) cells. J Virol. 66:4180-4190, 1992.
43. Condreay L D, Brown D T. Exclusion of superinfecting homologous virus by Sindbis virus-infected Aedes albopictus (mosquito) cells. J Virol. 58:81-86, 1986.
44. Condreay L D, Brown D T. Suppression of RNA synthesis by a specific antiviral activity in Sindbis virus-infected Aedes albopictus cells. J Virol. 62:346-348, 1988
45. Menard S, Tagliabue E, Colnaghi M N The 67 kDa laminin receptor as a prognostic factor in human cancer. Breast Cancer Res. Treat 52:137-145, 1998
46. Paolo Viacava, Antonio G. Naccarato, Paola Collecchi, Sylvie Menard, Vincent Castronovo and Generoso Bevilacqua. The Spectrum Of 67-Kd Laminin Receptor Expression. In Breast Carcinoma Progression Journal of Pathology 182: 3644, 1997.
47. Martignone S, Menard S, Bufalino R, Cascinelli N, Pellegrini R, Tagliabue E, Andreola S, Rilke F, Colnaghi MI. Prognostic significance of the 67-kilodalton laminin receptor expression in human breast carcinomas. J Natl. Cancer Inst. 85:398-402, 1993.
48. Basolo F, Pollina L, Pacini F, Fontanini G, Menard S, Castronovo V, Bevilacqua G. Expression of the Mr 67,000 laminin receptor is an adverse prognostic indicator in human thyroid cancer: an immunohistochemical study. Clin. Cancer Res. 2:1777-1780, 1996.
49. Sanjuan X, Fernandez P L, Miquel R, Munoz J, Castronovo V, Menard S, Palacin A, Cardesa A, Campo E. Overexpression of the 67-kD laminin receptor correlates with tumor progression in human colorectal carcinoma J Pathol. 179:376-380, 1996.
50. de Manzoni G, Verlato G, Tomezzoli A, Guglielmi A, Pelosi G, Ricci F, Di Leo A, Cordiano C. Study on Ki-67 immunoreactivity as a prognostic indicator in patients with advanced gastric cancer. Jpn J Clin. Oncol. 28:534-537, 1998.
51. Pelosi G, Pasini F, Bresaola E, Bogina G, Pederzoli P, Biolo S, Menard S, Zamboni G. High-affinity monomeric 67-kD laminin receptors and prognosis in pancreatic endocrine tumors. J Pathol. 183:62-69, 1997.
52. van den Brule F A, Castronovo V, Menard S, Giavazzi R, Marzola M, Belotti D, Taraboletti G Expression of the 67 kD laminin receptor in human ovarian carcinomas as defined by a monoclonal antibody, MluC5. Eur J Cancer 32A:1598-1602, 1996.
52. Griffin D E and J M Hardwick. Regulators of apoptosis on the road to persistent alphavirus infection. Ann. Rev. Microbiol. 51:565-592, 1997.
53. Taraboletti G, Belotti D, Giavazzi R, Sobel M E, Castronovo V. Enhancement of metastatic potential of murine and human melanoma cells by laminin receptor peptide G: attachment of cancer cells to subendothelial matrix as a pathway for hematogenous metastasis. J Natl. Cancer Inst. 85:235-240, 1993.
54. Ozaki I, K Yamamoto, T Mizuta, S Kajihara, N Fukushima, Y Setoguchi, F Morito, T Sakai. Differential expression of laminin receptors in human hepatocellular carcinoma. Gut 43:837-842, 1998.
55. van den Brule F A, Buicu C, Berchuck A, Bast R C, Deprez M, Liu F T, Cooper D N, Pieters C, Sobel M E, Castronovo V Expression of the 67-kD laminin receptor, galectin-1, and galectin-3 in advanced human uterine adenocarcinoma. Hum Pathol 27:1185-1191, 1996.
55. Bosma M, Schuler W, Bosma G. The scid mouse mutant. Curr Top Microbiol Immunol 137:197-202, 1988.
56. Lacal J C, Vazquez D, Fernandez-Sousa J M, Carrasco L Antibiotics that specifically block translation in virus-infected cells. J Antibiot (Tokyo) 33:441-446, 1980
57 Wang K S, Kuhn R J, Strauss E G, Ou S, Strauss J H. High-affinity laminin receptor is a receptor for Sindbis virus in mammalian cells. J Virol 66:4992-5001, 1992.
58. Strauss J H, Wang K S, Schmaljohn A L, Kuhn R J, Strauss E G. Host-cell receptors for Sindbis virus. Arch Virol. Suppl. 9:473-484, 1994.
59. Liotta, L. A. 1986. Tumor Invasion and Metasteses—Role of the Extracellular Matrix: Rhoads Memorial Award Lecture. Cancer Research 46:1-7.
60. Aznavoorian, S. Murphy, A. N., Stetler-Stevenson, W. G., and Liotta, L. A. 1992. Molecular Aspects of Tumor Cell Invasion and Metastasis, pp. 1368-1383.
61. Wewer U M, Liotta L A, Jaye M, Ricca G A, Drohan W N, Claysmith A P, Rao C N, Wirth P, Coligan J E, Albrechtsen R, Mudry M and Sobel M E. Altered levels of laminin receptor mRNA in various human carcinoma cells that have different abilities to bind laminin. Proc. Natl. Acad. Sci. USA 83; 7137-7141, 1986.
62. Hand P H, Thor A, Schlom J, Rao C N and Liotta L. Expression of laminin receptor in normal and carcinomatous human tissues as defined by a monoclonal antibody. Cancer Res. 45; 2713-2719, 1985.
63. Liotta L A, Horan Hand P, Rao C N, Bryant G, Barsky S H, Schlom J. Monoclonal antibodies to the human laminin receptor recognize structurally distinct sites. Exp Cell Res. 156:117-26, 1985.
64. Barsky S H, Rao C N, Hyams D, Liotta L A. Characterization of a laminin receptor from human breast carcinoma tissue. Breast Cancer Res Treat. 4:181-188, 1984.
65. Wewer U M, Taraboletti G, Sobel M E, Albrechtsen R and Liotta L A. Role of laminin receptor in tumor cell migration. Cancer Res. 47; 5691-5698, 1987.
66. Terranova V P, Rao C N, Kalebic T, Margulies I M, Liotta L A. Laminin receptor on human breast carcinoma cells. Proc Natl Acad Sci USA. 80:444-448, 1983.
67. Wang K S, Kuhn R J, Strauss E G, Ou S, Strauss J H. High-affinity laminin receptor is a receptor for Sindbis virus in mammalian cells. J Virol. 66:4992-5001, 1992.
68. Kozlowski J M et al. Metastatic behavior of human tumor cell lines growth in the nude mouse. Cancer Res. 44; 3522-3529, 1984.
69. Hurlbut, H. S. "The experimental transmission of coxsackie-like viruses by mosquitoes." J. Egypt. Med. Assoc. 36: 495-498, 1953.
70. Luo T, Brown D T.Purification and characterization of a Sindbis virus-induced peptide which stimulates its own production and blocksvirus RNA synthesis. Virology. 194:44-49, 1993.
71. Riedel B, Brown D T.Novel antiviral activity found in the media of Sindbis virus-persistently infected mosquito (Aedes albopictus) cellcultures.J Virol. 29:51-60, 1979.
72. Miller, M. L. and Brown, D. J. "Morphogenesis of Sindbis Virus in Three Subclones of Aedes Albopictus (Mosquito Cells)" J. Virol. 66: 4180-4190, 1992
73. Karpf, A. R. and Brown, D. T. "Comparison of Sindbis Virus-Induced Pathology in Mosquito and Vertebrate Cell Cultures", Virol. 240, 193-201 (1998)
74. Bieganski, R. M., et al "Stabilization of active recombinant retroviruses in an amorphous dry state with trehalose", Biotechnol. Prog. 1998 July-August; 14(4):615-20
75. Croyle, M. A. et al "Factors that influence stability of recombinant adenoviral preparations for human gene therapy", Pharm. Dev. Technol. 1998 August; 3(3):373-83
76. Kotani, H. et al "Improved methods of retroviral vector transduction and production for gene therapy", Hum. Gene Ther. 1994 January; 5(1): 19-28
77. Cichon G. et al., "Intravenous administration of recombinant adenoviruses cases thrombocytopenia, anemia and erythroblastosis in rabbits", J Gene Med 1999, September-October;(5):360-71
78. Douglas et al "A Role for Sp1 in the Transcriptional Regulation of Hepatic Triacylglyerol Hydrolase in the Mouse", J. of Biological Chem. 2001 July; 276(27): 25621-25630

We claim:

1. A packaging cell line for the continuous production of alphavirus vectors comprising:
an insect cell selected from cells having the apoptosis resistance properties of mosquito cells to Sindbis virus transfected with DNA encoding alphavirus structural proteins, replicase, and DNA encoding an alphavirus replicon comprising a gene encoding a protein of interest with an alphavirus packaging signal, wherein expression of said proteins, replicase, and replicon are driven by strong insect promoters and said cell line continuously produces alphavirus viral vectors at a high titer.

2. The cell line of claim 1 wherein said insect cell is a mosquito cell.

3. The cell line of claim 1 wherein said alphavirus is a Sindbis virus.

4. The cell line of claim 1 wherein said promoter is an OpIE2 promoter.

5. The cell line of claim 2 wherein said mosquito cell is stably transformed with DNA encoding the Sindbis virus genes required for the production of Sindbis viral vectors.

6. The cell line of claim 5 wherein said genes are encoded on at least a first and a second plasmid.

7. The cell line of claim 6 wherein said first plasmid encodes the replicon comprising the Sindbis virus packaging signal, non-structural proteins NSP1-4 and a gene of interest.

8. The cell line of claim 6 wherein said second plasmid encodes genes for Sindbis virus structural proteins.

9. The cell line of claim 8 wherein said structural proteins comprise capsid, E1, E2, E3 and 6K.

10. A method for producing alphavirus vectors comprising the steps of:
  (a) incubating insect cells selected from cells having the apoptosis resistant properties of mosquito cells to Sindbis virus transfected with DNA encoding alphavirus structural proteins, replicase, and an alphavirus replicon comprising a gene encoding a protein of interest with an alphavirus packaging signal in an appropriate selective media; and
  (b) collecting alphavirus vectors secreted into the media, wherein said genes are driven by strong insect promoters and said cell line continuously produces alphavirus viral vectors at a high titer.

11. The method of claim 10 wherein said alphavirus is a Sindbis virus.

12. The method of claim 10 wherein said insect cell is a mosquito cell.

13. The method of claim 10 wherein said promoter is an OpIE2 promoter.

14. The method of claim 12 wherein said mosquito cell is stably transformed with DNA encoding the Sindbis virus genes required for the productions of Sindbis virus vectors.

15. The method of claim 14 wherein said genes are encoded on at least a first and a second plasmid.

16. The method of claim 15 wherein said first plasmid encodes RNA comprising the Sindbis virus packaging signal, non-structural proteins NSP1-4 and the gene of interest.

17. The method of claim 15 wherein said second plasmid encodes genes for Sindbis virus structural proteins.

18. The method of claim 17 wherein said structural proteins comprise capsid, E1, E2, E3 and 6K.

19. A vector construct comprising a sequence encoding a Sindbis virus replicon peratively associated with a strong insect promoter, which replicon comprising a gene of interest with a packaging signal.

20. The vector construct of claim 19 which is a plasmid.

21. The vector construct of claim 19, wherein said promoter is an OpIE2 promoter.

22. The vector construct of claim 19, wherein the Sindbis virus replicon comprises a Sindbis virus packaging signal, non-structural proteins NSP1-4, and the gene of interest.

23. A vector construct comprising a sequence encoding a Sindbis virus structural protein operatively associated with a strong insect promoter.

24. The vector construct of claim 23 which is a plasmid.

25. The vector construct of claim 23, wherein the structural protein is capsid protein.

26. The vector construct of claim 25, further comprising sequences encoding Sindbis virus structural proteins E1, E2, E3, and 6K, which sequences are operatively associated with a strong insect promoter.

27. The vector construct of claim 23, which comprising sequences encoding Sindbis virus structural proteins E1, E2, E3, and 6K, which sequences are operatively associated with a strong insect promoter.

28. The vector construct of claim 23, wherein said promoter is an OpIE2 promoter.

* * * * *